US008753310B2

(12) United States Patent
Sullivan et al.

(10) Patent No.: US 8,753,310 B2
(45) Date of Patent: Jun. 17, 2014

(54) RECONSTITUTING INFUSION DEVICE

(75) Inventors: Vincent J. Sullivan, Cary, NC (US); Ge Jiang, Thousand Oaks, CA (US); Matthew S. Ferriter, Chapel Hill, NC (US); Kenneth G. Powell, Raleigh, NC (US); P. Spencer Kinsey, Vernon, CT (US); Carl R. Sahi, Coventry, CT (US); John M. Polidoro, Coventry, CT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 177 days.

(21) Appl. No.: 13/185,492

(22) Filed: Jul. 18, 2011

(65) Prior Publication Data
US 2011/0270223 A1 Nov. 3, 2011

Related U.S. Application Data

(62) Division of application No. 11/222,204, filed on Sep. 8, 2005, now Pat. No. 7,981,076.

(60) Provisional application No. 60/609,081, filed on Sep. 10, 2004.

(51) Int. Cl.
*A61M 37/00* (2006.01)
(52) U.S. Cl.
USPC .......... 604/84; 604/82; 604/87; 604/88; 604/92
(58) Field of Classification Search
USPC .......... 604/82, 86–88, 92, 131, 134, 191
See application file for complete search history.

(56) References Cited

U.S. PATENT DOCUMENTS

| 3,490,437 | A | 1/1970 | Bakondy et al. |
| 4,031,892 | A | 6/1977 | Hurschman et al. |
| 4,180,070 | A | 12/1979 | Genese |
| 4,552,561 | A | 11/1985 | Eckenhoff et al. |
| 5,041,088 | A | 8/1991 | Ritson et al. |
| 5,045,064 | A | 9/1991 | Idriss |
| 5,085,651 | A | 2/1992 | Py |
| 5,116,316 | A | 5/1992 | Sertic |

(Continued)

FOREIGN PATENT DOCUMENTS

| DE | 4039191 | 11/1991 |
| GB | 2015340 | 9/1979 |

(Continued)

OTHER PUBLICATIONS

International Search Report from PCT/US2005/031658.

(Continued)

*Primary Examiner* — Emily Schmidt
(74) *Attorney, Agent, or Firm* — Roylance, Abrams, Berdo & Goodman, L.L.P.

(57) ABSTRACT

A system and method for a patch-like, self-contained multi-component substance infusion device which provides one or more substantially hidden patient needles which can be placed in fluid communication with a fluid reservoir assembly that includes a rigid bladder portion used in conjunction with a non-distensible bladder film, such as a metallized film. The device can be attached to a skin surface via an adhesive contact and a pressurization system provides a pressure to the contents of a fluid reservoir assembly. Improvements to dry powdered formulations for reconstitution for preferred use in the device are also disclosed.

13 Claims, 18 Drawing Sheets

(56) References Cited

U.S. PATENT DOCUMENTS

| | | |
|---|---|---|
| 5,304,163 A | 4/1994 | Bonnici |
| 5,336,180 A * | 8/1994 | Kriesel et al. .................... 604/82 |
| 5,423,421 A * | 6/1995 | Inoue et al. .................... 206/219 |
| 5,554,131 A | 9/1996 | Lacivita |
| 5,649,910 A | 7/1997 | Kriesel |
| 5,716,343 A | 2/1998 | Kriesel |
| 5,752,940 A | 5/1998 | Grimard |
| 5,779,668 A | 7/1998 | Grabenkort |
| 5,779,676 A | 7/1998 | Kriesel et al. |
| 5,814,020 A | 9/1998 | Gross et al. |
| 5,891,086 A | 4/1999 | Weston |
| 5,957,895 A | 9/1999 | Sage et al. |
| 6,045,254 A | 4/2000 | Inbar et al. |
| 6,063,068 A | 5/2000 | Fowles |
| 6,090,071 A | 7/2000 | Kriesel et al. |
| 6,099,504 A | 8/2000 | Gross et al. |
| 6,349,850 B1 | 2/2002 | Cheikh |
| 6,423,037 B1 | 7/2002 | Hijikata et al. |
| 6,478,771 B1 | 11/2002 | Lavi et al. |
| 6,589,229 B1 | 7/2003 | Connelly et al. |
| 6,656,147 B1 | 12/2003 | Wilkinson et al. |
| 6,673,038 B2 | 1/2004 | Weston |
| 6,689,108 B2 | 2/2004 | Lavi et al. |
| 6,702,779 B2 | 3/2004 | Connelly et al. |
| 6,723,068 B2 | 4/2004 | Lavi |
| 6,730,328 B2 | 5/2004 | Maskiewicz et al. |
| 6,780,171 B2 | 8/2004 | Gabel et al. |
| 6,802,813 B2 | 10/2004 | Schutt |
| 7,047,070 B2 | 5/2006 | Wilkinson et al. |
| 7,115,108 B2 | 10/2006 | Wilkinson et al. |
| 7,135,180 B2 | 11/2006 | Truong-Le |
| 7,214,221 B2 | 5/2007 | Fentress et al. |
| 7,250,037 B2 | 7/2007 | Shermer et al. |
| 7,364,446 B2 | 4/2008 | Kurashima |
| 7,374,744 B2 | 5/2008 | Schutt |
| 7,627,938 B2 | 12/2009 | Kim et al. |
| 7,736,333 B2 | 6/2010 | Gillespie |
| 7,850,663 B2 | 12/2010 | Sullivan et al. |
| 2001/0047162 A1 * | 11/2001 | Yugari .................... 604/410 |
| 2004/0005310 A1 | 1/2004 | Rapp |
| 2004/0092470 A1 | 5/2004 | Leonard et al. |
| 2005/0013867 A1 | 1/2005 | Lehrman et al. |
| 2005/0065472 A1 | 3/2005 | Cindrich et al. |
| 2005/0180952 A1 | 8/2005 | Pettis et al. |

FOREIGN PATENT DOCUMENTS

| | | |
|---|---|---|
| JP | 2002529204 A | 9/2002 |
| JP | 2003277287 A | 10/2003 |
| JP | 2004232883 A | 8/2004 |
| WO | WO9720536 | 6/1997 |
| WO | WO03087327 A2 | 10/2003 |
| WO | WO2004032990 | 4/2004 |

OTHER PUBLICATIONS

International Search Report from PCT/US2005/031658, a related PCT application of the Instant Application.

* cited by examiner

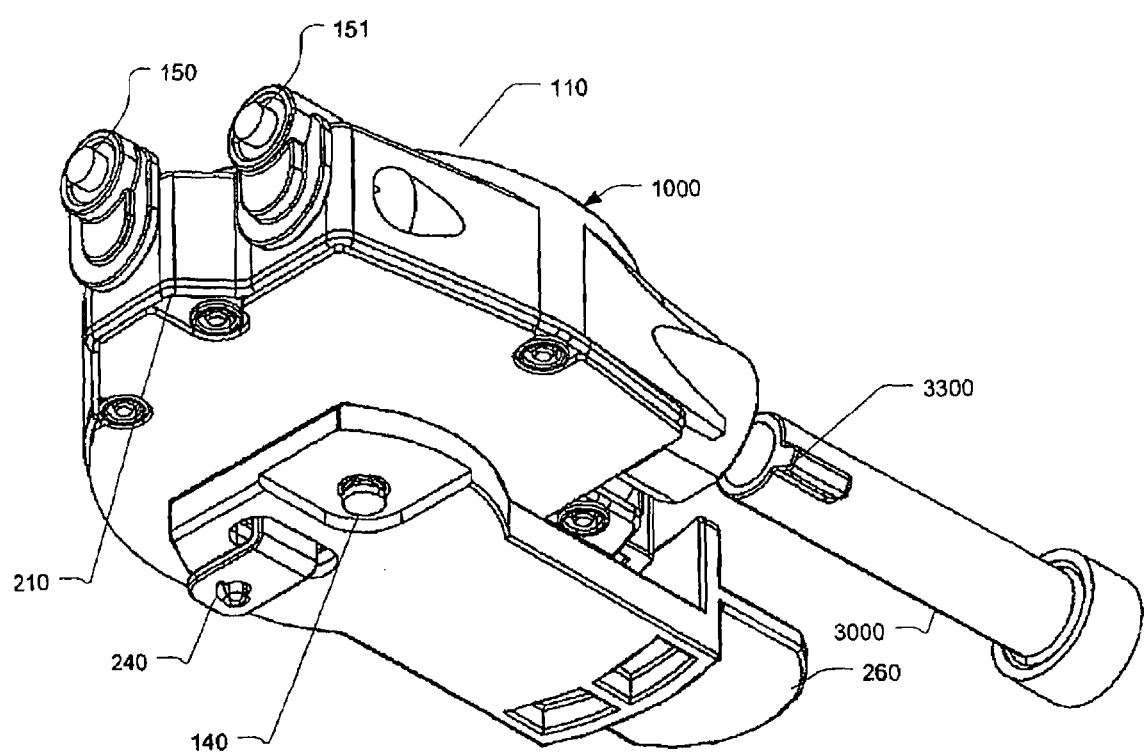

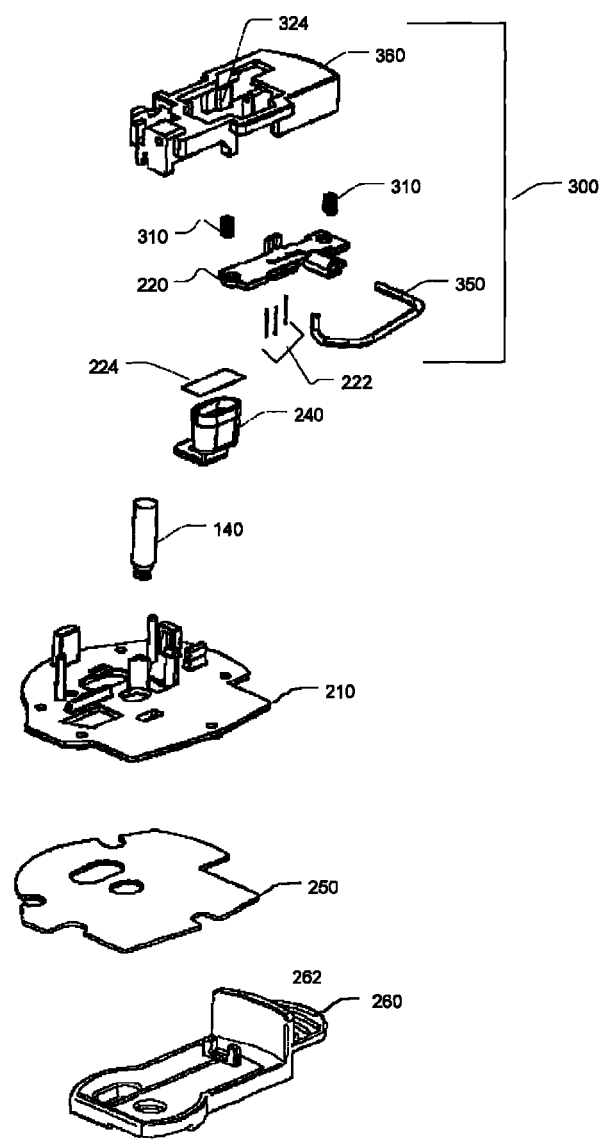

RECONSTITUTING INFUSION DEVICE

CROSS-REFERENCE TO RELATED APPLICATIONS

This application is a division of U.S. Non-Provisional patent application Ser. No. 11/222,204, filed Sep. 8, 2005 now U.S. Pat. No. 7,981,076 in the U.S. Patent and Trademark Office, which claims priority to provisional application Ser. No. 60/609,081, filed on Sep. 10, 2004, the disclosures of both applications being incorporated herein by reference in their entirety.

This application contains subject matter related to that of U.S. non-provisional patent applications of Shermer et al., entitled "Patch-Like Infusion Device", Ser. No. 10/623,702, filed on Jul. 22, 2003, now U.S. Pat. No. 7,250,037, and Cindrich et al., entitled "Patch-Like Infusion Device", Ser. Nos. 10/916,649 and 10/916,648, filed on Aug. 12, 2004, the latter now issued as U.S. Pat. No. 7,857,131, the entire contents of all of which are incorporated herein by reference in their entirety.

FIELD OF THE INVENTION

The present invention relates generally to medical devices and methods for the preparation and administration of therapeutic or other compounds to a patient, and more particularly to drug reconstitution and administration systems and methods which facilitate optimal reconstitution, mixing and dilution of a drug and/or other compound with a liquid diluent, and subsequent administration of the resultant mixture from an infusion type device.

BACKGROUND OF THE INVENTION

Infusion therapy is a widely known therapy for patients who require medicaments to be delivered over some time period. Diabetic infusion pump therapy, which entails the purchase of an expensive pump that lasts for about three years, has possibly the largest population of outpatient infusion therapy. The initial cost of the pump is a high barrier to this type of therapy. From a user perspective, however, the overwhelming majority of patients who have used pumps prefer to remain with pumps for the rest of their lives. This is because infusion pumps, although more complex than syringes and pens, offer the advantages of continuous infusion of insulin, precision dosing and programmable delivery schedules. This results in closer glucose control and an improved feeling of wellness.

As patients on oral agents eventually move to insulin and their interest in intensive therapy increases, users typically look to insulin pumps. However, in addition to their high cost (roughly 8 to 10 times the daily cost of syringe therapy) and limited lifetime, insulin pumps represent relatively old technology and are cumbersome to use. Also, from a lifestyle standpoint, the tubing (known as the "infusion set") that links the pump with the delivery site on the user's abdomen is very inconvenient and the pumps are relatively heavy, making carrying the pump a burden.

Therefore interest in better therapy is on the rise, accounting for the observed growth in pump therapy and increased number of daily injections. In this and similar infusion examples, what is needed to fully meet this increased interest is a form of insulin delivery or infusion that combines the best features of daily injection therapy (low cost and ease of use) with those of the insulin pump (continuous infusion and precision dosing) and that also avoids the disadvantages of each.

Several attempts have been made to provide ambulatory or "wearable" drug infusion devices that are low in cost and convenient to use. Some of these devices are intended to be partially or entirely disposable. In theory, devices of this type can provide many of the advantages of an infusion pump without the attendant cost and inconvenience. Unfortunately, however, many of these devices suffer from disadvantages including user discomfort (due to the gauge and/or length of injection needle used), compatibility and interaction between the substance being delivered and the materials used in the construction of the infusion device, and possible malfunctioning if not properly activated by the user (e.g., "wet" injections resulting from premature activation of the device). Long-term drug stability has also been an issue for these types of devices, and therefore a majority of drugs, when in liquid form must be refrigerated.

In order to combat the drug stability problem, storage-stability can be imparted to medicaments by placing them in a dry powder form. Techniques for doing this include freeze-drying, spray freeze-drying, lyophilization and the like. However, reconstitution of such medicaments has been difficult and involves many steps. Additionally, reconstituted liquids typically do not have the same properties as a liquid drug formulation, at least because bubbles may be formed during reconstitution.

Various methods to disrupt bubbles in reconstituted formulations have been attempted in the past. Most of these methods use application of ultrasonic energy. The ultrasonic effect is based on what is known as cavitation, i.e., cavities containing gas formed by sound waves. These cavities collide with each other forming larger cavities that then rise to the surface and dissipate. These methods require specialized and bulky equipment and power sources. Yet another drawback of cavitation is the momentary, yet intense, burst of heat generated as each bubble collapses. The heat generated can certainly destroy some active components or unstable drugs in the product. It would be desirable to have a method for removing bubbles from a reconstituted solution, which did not have such issues as high-energy input and heat generation. Other methods to reduce bubble formation that have been attempted are application of a high pressure. It is theorized that high pressures reduces bubble formation because the rate of bubble collapse is proportional to G, the gradient between external tension and bubble internal pressure. The higher external tension can shrink bubbles. With a decrease in diameter of the bubbles, the increased internal gas pressure forces the gas inside the bubble to dissolve, resulting in bubble collapse as the gas is forced into solution. Nevertheless, this approach also requires additional equipment safeguards and is not feasible for many applications due to either safety or cost concerns. Additionally, a bubble will form again after high pressure is removed, such as when the reconstituted product is drawn out of a pressured vial.

To date, however, there remains a need for a system for the administration of medicaments where the medicament is in a storage stable dry form, which can be readily reconstituted and directly administered via an infusion type device. Additionally, the reconstituted drug should have properties, which mimic the pre-mixed liquid formulation. Accordingly, a need exists for an alternative to current infusion devices, such as infusion pumps for insulin that further provides simplicity in manufacture and ease-of-use for both insulin and non-insulin applications.

SUMMARY OF THE INVENTION

The present drug reconstitution and administration system is a multi-component arrangement normally enclosed within a housing which permits a concentrated drug or other composition to be mixed with a liquid diluent from a pre-filled cartridge assembly, with the system further permitting the infuser reservoir to be filled with the resultant mixture for patient administration. The system permits drugs to be efficiently stored and handled in concentrated form, and further facilitates dilution or reconstitution of the drugs to the desired concentration just prior to administration through the use of the integrated components of the system.

In accordance with the illustrated embodiments, the present system includes a container, or cartridge for containing a drug or other medicament, with the container having a pierceable stopper for closing the container. The system further includes an infuser assembly including a reservoir having a filling end, and a patient needle end defining a flow passage therebetween. The reservoir defines an internal chamber in fluid communication with the flow passage so that liquid can be moved into and out of the internal chamber via the flow passage. The reservoir may be constructed in accordance with the reservoir construction of U.S. patent application of Cindrich et al., Ser. Nos. 10/916,649 and 10/916,648, filed on Aug. 12, 2004, the entire content of which is incorporated herein by reference.

The present system further includes a mixing adapter assembly for mixing a liquid in the reservoir assembly with a medicament in the cartridge. The adapter assembly includes a generally cylindrical receiving inlet having an access needle for fluid connection with the pierceable stopper of the associated cartridge. By this arrangement, the end of the cartridge, and the stopper positioned therein, can be positioned in one end of the receiving inlet sleeve of the adapter assembly. The receiving inlet has an inside diameter larger than the outside diameter of the associated cartridge, thus permitting the cartridge assembly to be positioned generally telescopically within the receiving inlet during use of the system.

The access needle of the receiving inlet and the cartridge assembly connect to the flow passage of the reservoir assembly and the patient needle in selective fluid communication with each other. Optionally, a valve is placed in the fluid path between the patient needle and the reservoir. By this arrangement, the present system permits reconstitution of a concentrated drug by positioning the drug filled cartridge assembly generally within the open end of the receiving inlet with the components slidably engaged to each other. In this configuration, a liquid, such as a diluent, pre-filled in the internal chamber of the reservoir assembly, can be caused to flow through the flow passage of access needle into the cartridge assembly by action of a low-pressure condition in the cartridge assembly. The reconstitution is effected by the diluent becoming in contact with the drug. The cartridge assembly is then slid longitudinally further into the receiving inlet, however, the stopper is prevented from further translation due to the interaction with the access needle hub. Thus the stopper is fixed in relation to the housing and is now translated with respect to the cartridge assembly such that the stopper forces the now drug/diluent mixture from the internal chamber of the cartridge and through the access needle into the reservoir assembly. The liquid from the reservoir assembly is thus mixed with the medicament from the cartridge within the chamber of the cartridge, and forced under pressure back into the reservoir assembly. The desired diluted drug mixture is thus provided within the now filled reservoir assembly, with the now-empty chamber fitted within the receiving inlet.

When mixing is complete, the present system facilitates administration of the mixture by methods and devices according to U.S. patent application of Cindrich et al., Ser. Nos. 10/916,649 and 10/916,648, filed on Aug. 12, 2004, the entire content of which is incorporated herein by reference. A general description of the action of the infuser is as follows: The device is self-contained and is attached to the skin surface of the user by adhesive disposed on a bottom surface. Once properly positioned and activated by the user, a pressurizing system acts on a reservoir surface within the device can be used to empty the contents of the partially flexible reservoir through one or more patient needles via a needle manifold. The substance within the reservoir is then delivered through the skin of the user by the needles, which are driven into the skin. It will be understood that other embodiments are possible in which the pressurizing system is replaced with a different type of energy device, which may be mechanical, electrical and/or chemical in nature inter alia gas generation pressurizing means, mechanical actuators, or shape memory alloys.

In the preferred form, the reservoir assembly is provided in a closed form to maintain its sterility, such as by the preferred provision of a blister package with pair of peel-away seals or like closing elements positioned at respective opposite ends of the adapter assembly. The arrangement is preferably configured for single-use, and to this end, a locking arrangement is provided which prevents removal of the cartridge from the adapter assembly after it has been connected with the receiving inlet.

Additionally, it has been found that pressure treatments of the medicament within the cartridge have an unexpected benefit to the quality of the reconstituted drug/diluent solution. For example, low pressure conditions in the drug reservoir not only serve the purpose of filling the cartridge with the diluent upon fluid connection to the reservoir, the resultant mixture has a lower observable amount of bubbles. Additionally in certain applications, it may be desirable to replace the atmospheric gasses normally present with the drug in the cartridge with inert gasses, inter alia argon, helium to further improve the reconstitution characteristics.

These and other aspects of the invention are substantially achieved by providing systems and methods for a patch-like, wearable, self-contained reconstituted substance infusion device which provides one or more substantially hidden patient needles which can be placed in fluid communication with a content reservoir assembly that includes a rigid bladder portion used in conjunction with a non-distensible bladder film, such as a metallized film. A connection is provided for a reconstitution fluid and/or dry powdered drug. A push type activation assembly is provided which can then be used to remove a retaining pin and allow a Disk spring assembly to apply an essentially even and constant pressure to the contents of a reservoir assembly. The push type activation assembly then releases and seats one or more spring-loaded patient needles into the patient's skin and establishes a fluid communication path between the patient needles and the pressurized reservoir contents, thereby delivering an infusion of contents into the skin of the user. Upon completion and removal of the infusion device, a number of safety mechanisms can be engaged to cover the needles for disposal.

BRIEF DESCRIPTION OF THE DRAWINGS

The various objects, advantages and novel features of the preferred embodiments of the present invention will be more readily appreciated from the following detailed description when read in conjunction with the appended drawings, in which:

FIG. 1B is a bottom perspective view of the patch-like injector of FIG. 1A.

FIG. 2B is a second exploded view of the patch-like injector of FIG. 1A showing the button assembly, needle manifold and lower housing.

Throughout the drawings, like reference numerals will be understood to refer to like parts, components or structures.

DETAILED DESCRIPTION OF THE EXEMPLARY EMBODIMENTS

Figure 1A:
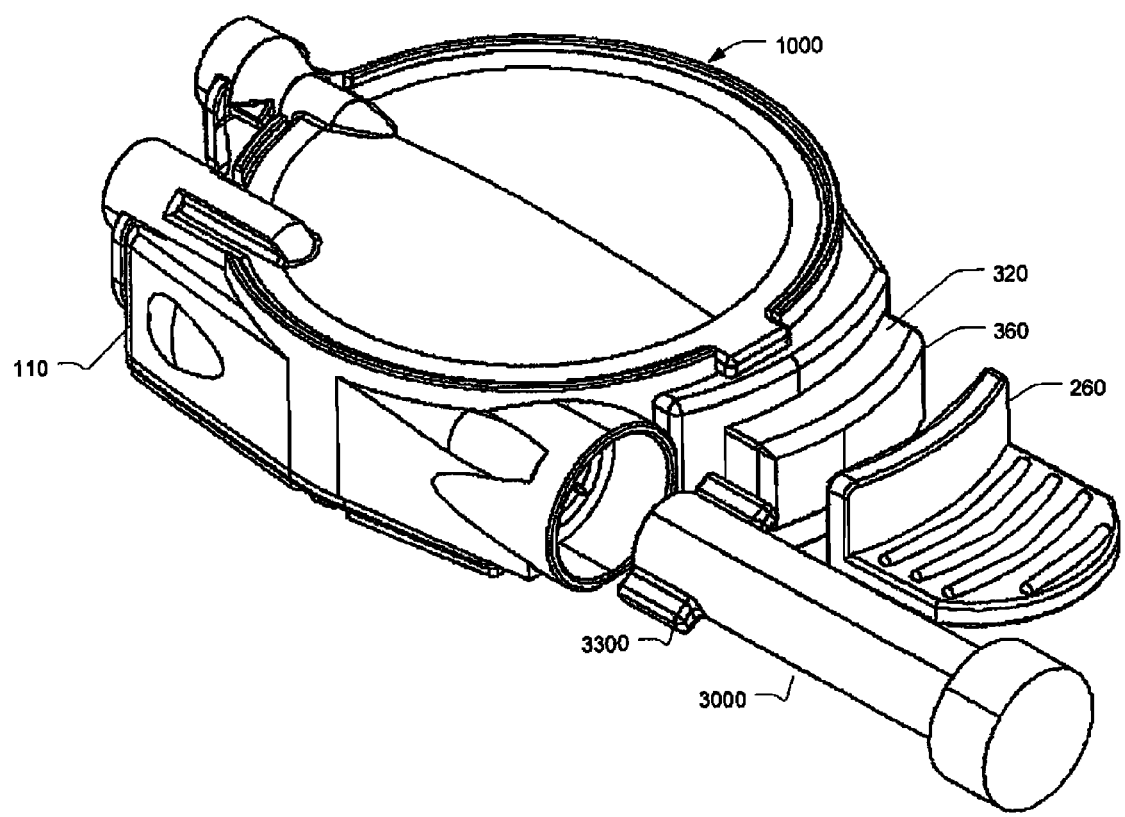
FIG. 1A is a top perspective view a patch-like injector or infusor system using a two component mixing system prior to activation.

The aspects of the present device described below can be used as a convenient, patch-like device to deliver a pre-measured dose of a substance, such as a drug or medication, which has been separated into at least two components (typically a liquid diluent, and a dry powder), to a user through an adhesive attached infusion device. The device is self-contained and is attached to the skin surface of the user by adhesive disposed on a bottom surface. Typically, the two components are mixed by the device and then transferred to the reservoir. Once properly positioned and activated by the user, a pressurization system on a reservoir surface within the device can be used to empty the contents of the partially flexible reservoir through one or more patient needles via a needle manifold. The mixed substance within the reservoir is then delivered through the skin of the user by the needles, which are driven into the skin.

It will be understood that other embodiments are possible in which the pressurization system is a variation of a disk spring, or different type of stored energy device, which may be mechanical, electrical and/or chemical in nature. It will also be understood that the terms mixing and reconstitution are used interchangeably herein when referring to the mixture of drug components in the cartridge and the reservoir. Medicament components to be mixed may be gasses, solids, liquids, dry powders, suspensions, or a mixture of any of these. Although many of the examples herein are of binary systems e.g. dry powder and diluent, it will be understood that multiple mixing operations may be performed so that more than two components may be mixed in a sequential fashion. As will be appreciated by one skilled in the art, there are numerous ways of carrying out the patch-like injection or infusor system disclosed herein. Although reference will be made to the embodiments depicted in the drawings and the following descriptions, the embodiments disclosed herein are not meant to be exhaustive of the various alternative designs and embodiments that are encompassed by the disclosed invention. In each disclosed embodiment, the device is referred to as an infusor; however, the device may also inject substances at a much faster bolus rate than is commonly accomplished by infusor devices. For example, the contents can be delivered in a period as short as several seconds, or as long as several days.

As shown in FIGS. 1A through 8D, the embodiment of certain aspects of present invention can be constructed to provide a patch-like, wearable, self-contained substance infusion device that can be used to deliver a variety of multiple-component medications to a patient e.g. dry powder and diluent. The device also provides for a separated drug container called a cartridge, which is filled with at least one component of the drug to be delivered to the patient. The device provides a hidden patient needle or needles prior to and during use, and can be secured to a patient via an adhesive surface. The pressurization of the contents of the reservoir can be achieved by removing or displacing the spring retention disk, as described in greater detail below, to pressurize the device contents and the device can then be further activated via a reasonable force applied to the top push surface to seat the patient needles. Alternatively, the patient may push on the side of the device to allow a mechanism to seat the needles. In doing so, the device facilitates self-injection and reduces or eliminates variations in injection techniques between users.

In an exemplary embodiment of aspects of the present invention shown in FIGS. 1A through 8D, an infusion device 1000 includes a reservoir subassembly 100, including an upper housing 110, a reservoir base surface 120, at least one Disk spring 130, a retaining pin 140, fill plug 150, septum 160 and reservoir film 170. The infusion device 1000 further includes a housing subassembly, including a lower housing 210, and patient needle manifold 220 having at least one patient needle 222 and a manifold film 224. The housing subassembly further includes a needle shield 230 and an adjustable needle cap 240. An adhesive layer 250 is disposed upon the lower surface of the lower housing 210, and can be covered by a removable film (not shown), and a pull handle 260. A clip, such as an "E" clip can be used to secure the retaining pin 140 to the pull handle 260. Alternatively, pin 140 may be integrally formed into pull handle 260. The infusion device 1000 further includes a push button subassembly 300, including at least one patient needle manifold drive spring 310, a push button slide 320, at least one septum needle 330, and a fluid communication tube 350. A button face 360 can be provided to complete the push button subassembly 300. The infusion device further includes cartridge assembly 3000, which contains a portion of the medicament to be delivered to the patient. Cartridge 3000 is inserted into housing 110. Subsequently, through a series of steps, medicament components in the reservoir 100 are mixed with medicament components in the cartridge 3000, and are finally deposited into the reservoir 100 for infusion into the patient via microneedles 222. According to one embodiment, the medicament component initially contained in the reservoir 100 is a fluid, e.g., a diluent, and the medicament component originally contained in the cartridge 3000 is a dry powder. According to another embodiment, the medicament component initially contained in the reservoir 100 is a dry powder and the medicament component originally contained in the cartridge 3000 is a fluid. According to yet another embodiment, both medicament components are fluids. Further, according to one embodiment, one of the medicament components is a liposome. In the description below, the term reservoir is often used to describe the assembled and separate reservoir base surface 120, fill plugs 150, 151, septums 160, 161 and reservoir film 170 of the reservoir subassembly 100.

FIG. 1A is a top perspective view of a first embodiment of the infusion device 1000. In FIG. 1A, the assembled upper and lower housing 110 and 210 respectively is shown, between which the push button subassembly 300 is contained. The pull handle 260, described in greater detail below, is shown in a pre-energized, pre-activated position and serves to secure the retaining pin 140 within the device and shield the push button 360 from any applied forces. As more clearly illustrated in FIG. 1B, which is a bottom perspective view of the first embodiment, the pull handle 260 is further interlocked with the needle cap 240 and the retaining pin 140 via clip 270. Also, the pull handle 260 is optionally further interlocked with the push button slide 320.

Figure 2A:
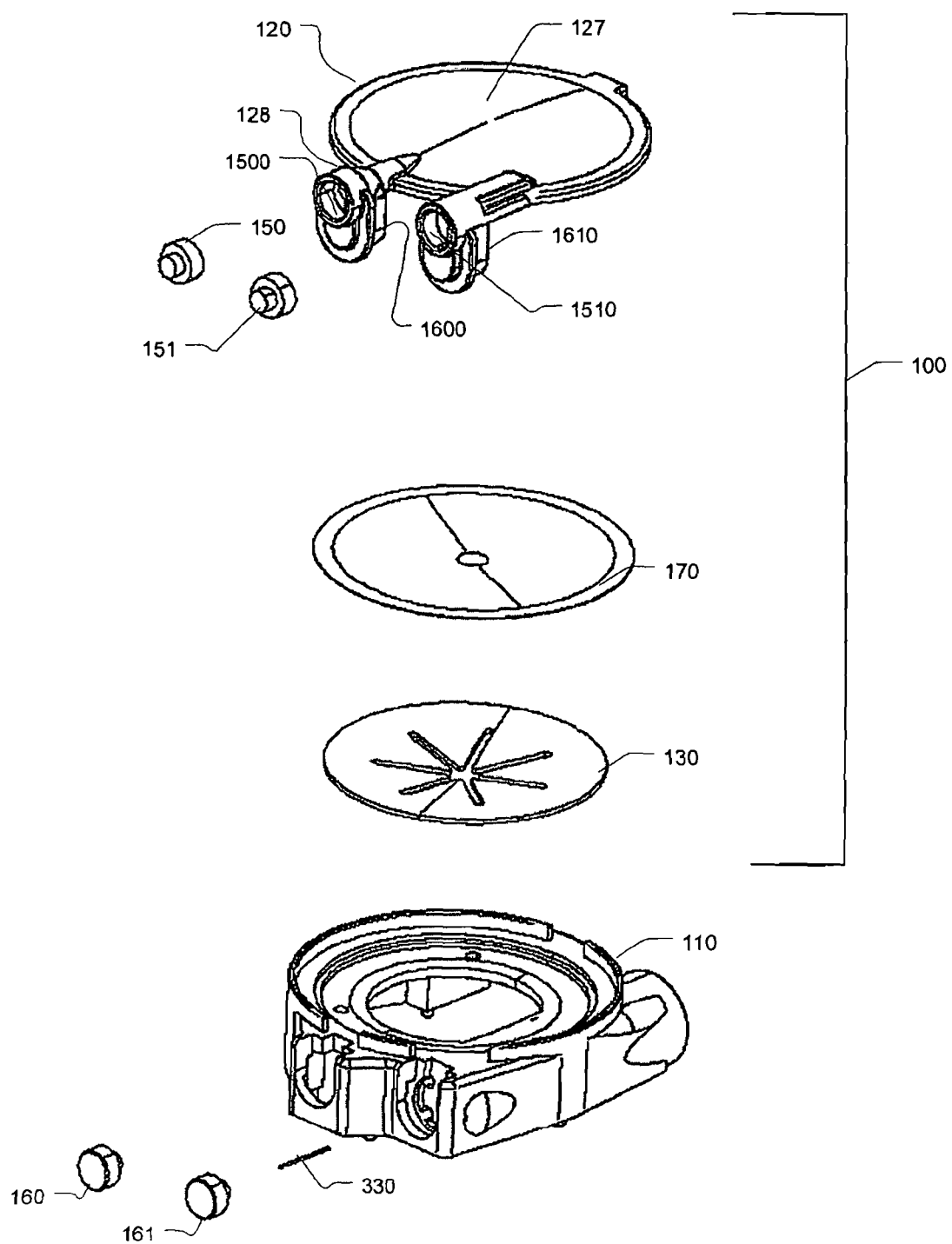
FIG. 2A is a first exploded view of the patch-like injector of FIG. 1A showing the reservoir assembly and upper housing.
Figure 2C:
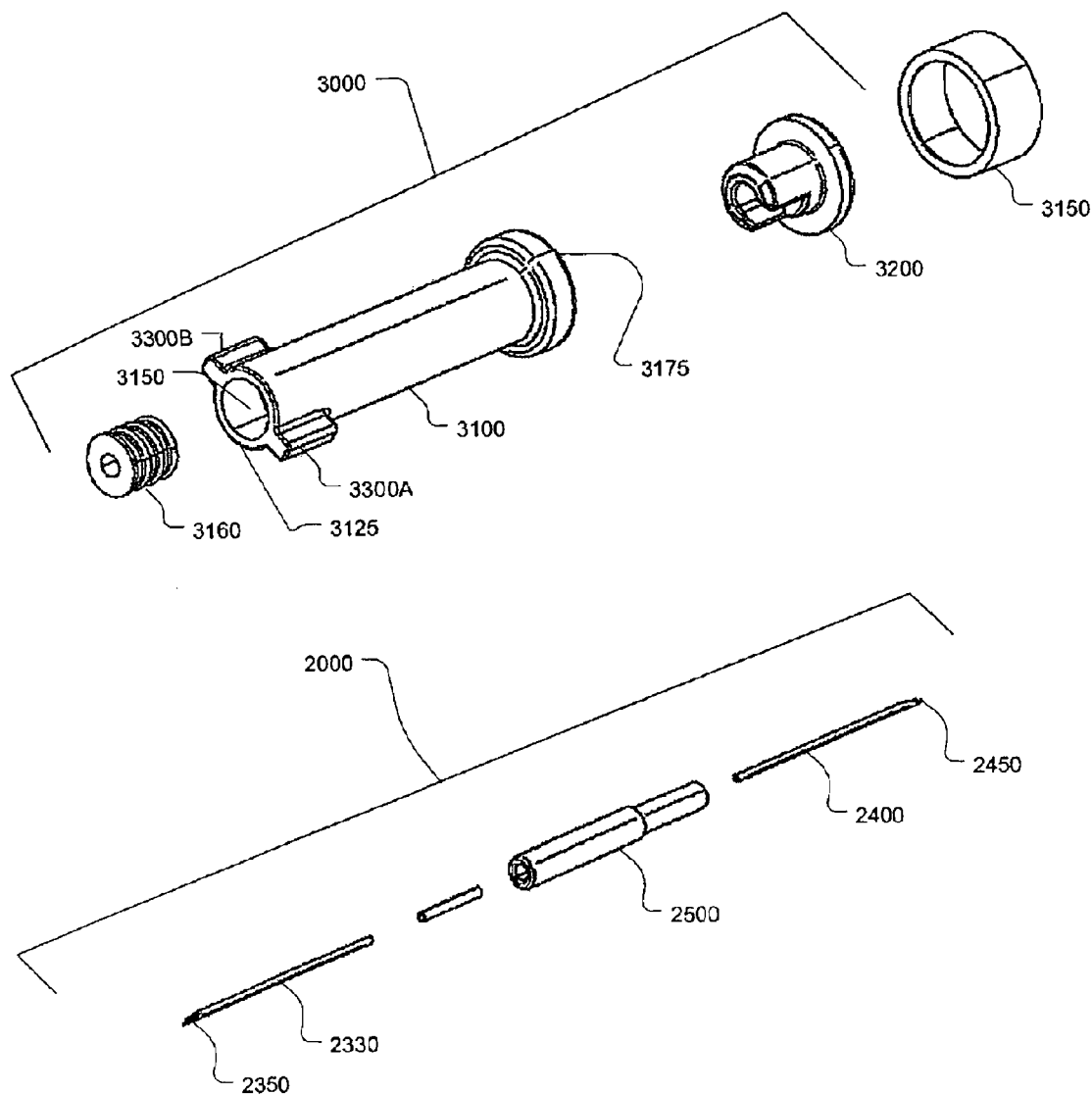
FIG. 2C is a third exploded view of the patch-like injector of FIG. 1A showing the cartridge assembly and access needle.

As shown in FIGS. 2A through 2C, the embodiment of the present invention 1000 can be constructed of these subassemblies to provide a patch-like, wearable, self-contained substance infusion device that can be used to deliver a variety of medications to a patient. The device 1000, shown in a pre-reconstitution, pre-energized, pre-activated position in FIG. 1A, provides a hidden patient needle or needles prior to and during use, and can be secured to a patient via an adhesive surface. The reconstitution of the finished drug to be delivered can be achieved by the insertion of cartridge 3000 into housing 110. The pressurization of the contents of the reservoir can be achieved by removing the pull handle 260 to "energize" the device and device contents, and the device can then be "activated" via a reasonable force applied to the push-button 360 to seat the patient needles and establish a flow path between the reservoir and needles. In doing so, the device 1000 facilitates self-injection and reduces or eliminates variations in injection techniques between users.

In FIG. 2A, the reservoir subassembly 100 of the infusion device 1000 is shown, and can be comprised of a rigid portion 120 used in conjunction with one or more non-distensible but flexible films 170, such as metallized films. The reservoir subassembly 100 can contain any number of substances between either a first and second film, where either the first or second film is also positioned against the rigid portion, or between a first film and the rigid portion. The reservoir is preferably filled with a liquid diluent. The rigid portion 120, or reservoir base, can be comprised of and serve as a hard portion of the reservoir against which the flexible film 170 can be pressed as described in greater detail below. As noted above, the reservoir of the embodiment shown in FIG. 2A can be constructed to preferably have a hard shell or inner surface, and at least one flexible film attached about the perimeter of the hard shell or inner surface. The flexible film 170 can be heat sealed to the rigid portion 120 to create a chamber, or bladder, for storage of device contents. As at least one wall of the chamber comprises a flexible film 170, and at least one wall of the chamber comprises a rigid surface, one or more Disk springs 130 can be placed adjacent to the flexible film 170 and used to apply a substantially constant pressure to the flexible film 170, and pressurize the reservoir chamber and contents. Although a disk spring is primarily disclosed, any type of pressurization system may be used with aspects of the invention. Septum 160 is inserted into rigid portion 120 at recess 1600 to seal the access path to microneedles 222, and septum 161 is inserted into rigid portion at recess 1610 to seal the access path to cartridge 3000. Additionally, fill plug 150 is inserted into recess 1500 and fill plug 151 is inserted into recess 1510 to provide closure of chamber 127 in reservoir 100.

The reservoir of the reservoir subassembly 100 is further preferably able to be stored for the prescribed shelf life of the reservoir contents in applicable controlled environments without adverse effect to the contents and is capable of applications in a variety of environmental conditions. Additionally, the barrier provided by the components of the reservoir do not permit the transport of gas, liquid and solid materials into or out of the contents at a rate greater than that allowable to meet the desired shelf life. In the embodiment shown in FIG. 2A, the reservoir subassembly materials are capable of being stored and operated in a temperature range of approximately 0 to 120 degrees F., and can have a shelf life of two or more years. Other variations of materials may be selected which allow for thermal cycles to room temperature and back to cold storage, as well as other temperature operating ranges, beyond 0 to 120 degrees F.

Now referring to FIG. 2C, which shows the cartridge assembly 3000. The cartridge assembly provides cartridge barrel 3100, which is prismatic in nature with a cylindrical cross-section, although any shape may be used. Cartridge barrel 3100 has a button end 3175 and an access end 3125, and an internal portion 3150. At the access end 3125 of cartridge body 3100 is fitted a slidable, pierceable stopper 3160. Stopper 3160 is slidably engaged to the internal diameter 3150 of cartridge barrel 3100. Stopper 3160 is slidable from access end 3125 to button end 3175. At the button end 3175 of cartridge barrel 3100 is plug 3200, which seals button end 3175 of cartridge barrel 3100. Cartridge barrel 3100 also has at least one tang 3300, and as shown in the drawings two tangs 3300A and 3300B. Tangs 3300 are provided for guiding cartridge 3000 into housing 110 and optionally for locking cartridge 3000 into housing 110 at the end of the mixing step. In an alternate embodiment, cartridge barrel 3100 is a test-tube like structure, with a single opening which forms the access end, thus eliminating the need for plug 3200. Optionally, plug cover 3170 covers plug 3200 for a more pleasing aesthetic appearance. In another alternate embodiment, cartridge barrel 3100 is an evacuated blood collection tube-like structure, with a single opening which forms the access end, and barrier properties which mimic evacuated blood collection tubes, thus eliminating the need for plug 3200. When assembled, the components of cartridge assembly 3000 form internal chamber 3500 which is contains a portion of the medicament to be mixed and delivered inter alia a dry powder.

The materials of the cartridge subassembly 3000 are further preferably able to be stored for the prescribed shelf life of the cartridge contents in applicable controlled environments without adverse effect to the contents. Additionally, the barrier provided by the components of the reservoir do not permit the transport of gas, liquid and solid materials into or out of the contents at a rate greater than that allowable to meet the desired shelf life. In the embodiment shown in FIG. 2C, the cartridge subassembly materials are capable of being stored and operated in a temperature range of approximately 0 to 120 degrees F., and can have a shelf life of two or more years. Preferably the cartridge subassembly is adapted to contain a vacuum for the entire shelf life of the system. Other variations of materials may be selected which allow for thermal cycles to room temperature and back to cold storage, as well as other temperature operating ranges, beyond 0 to 120 degrees F.

FIG. 2C also shows an exploded view of access needle assembly 2000 which is a hub having double pointed needle assembly. In this embodiment the double pointed needle assembly has separated stopper needle 2400 and septum needle 2330 affixed to hub 2500. In an alternate embodiment, access needle 2000 is formed from a single double pointed needle having a stopper end 2450 and a septum end 2350. Access needle 2000 is contained within and slidably engaged to housing 110. Stopper end 2450 is adapted to penetrate stopper 3160 and Septum end 2350 is adapted to penetrate septum 161. Access Needle 2000 provides for a selectable fluid conduit from the chamber 127 of reservoir 1000 to chamber 3500 of cartridge 3000.

The reservoir of the reservoir subassembly 100 is preferably evacuated prior to filling, as described in greater detail below. According to one embodiment, the pressure in the reservoir is greater than 2000 mT of vacuum. In addition, the shape of the reservoir may be configured to adapt to the type of energizing mechanism used, e.g., a disk or Belleville spring 130 having any number of diameters and height dimensions. Additionally, using an evacuated flexible reservoir during filling minimizes any air or bubbles within the filled reservoir. The use of a flexible reservoir is also very beneficial when the device is subjected to external pressure or temperature variations, which can lead to increased internal reservoir pressures. In such case, the flexible reservoir expands and contracts with the contents, thereby preventing possible leaks due to expansion and contraction forces exerted on the fill plugs 150, 151 and septum 160, 161. This also helps to eliminate dose variation due to temperature and pressure fluctuations in the environment. Additionally, a flexible reservoir ensures the ability of a vacuum in the cartridge to enable temporary filling of cartridge 3000 for reconstitution, and subsequent re-filling of reservoir 100. According to one embodiment, the pressure in the cartridge 3000 prior to communication with the reservoir is less than atmospheric pressure. According to one embodiment, the pressure in the cartridge 3000 prior to communication with the reservoir is between 2000 mT of vacuum and atmospheric pressure.

Yet another feature of the reservoir subassembly 100 includes the ability to permit automated particulate inspection at the time of fill, or by a user at the time of use. One or more reservoir barriers, such as the rigid portion 120, can be molded of a transparent, clear plastic material, which allows inspection of the substance contained within the reservoir. The transparent, clear plastic material is preferably a cyclic olefin copolymer that is characterized by high transparency and clarity, low extractables and biocompatibility with the substance contained in the reservoir.

The rigid portion 120 of the reservoir subassembly 100 of FIG. 2A further comprises at least one fluid path 128 as shown in FIG. 2A, which accesses the main chamber 127 of the reservoir. In the embodiment shown in FIG. 2A, the fluid path 128 exits the main chamber 127 of the reservoir, passing under or through the heat seal area provided about the perimeter of the rigid portion 120 for securing the flexible film 170, and into a chamber 129 between a fill-head stopper 150 and a septum 160, allowing fluid of the reservoir to travel from the reservoir to the septum 160. In the embodiment shown in FIG. 2A, the fluid path 128 is preferably constructed to reduce dead volume and incorporates a fill-head receiving geometry.

The septum 160 of FIG. 2A, is positioned between the first fluid path 128 and a second fluid path comprised of the septum needle 330, septum needle manifold 322, and tube 350, and can be an elastomeric plug that when penetrated by a septum spike or septum needle 330, creates a sterile flow path between the reservoir and the patient needles 222. The septum needle 330, which is used to penetrate the septum 160 and create a flow path between the first and second fluid paths, can include a septum needle boot that maintains the sterility of the septum needle prior to, and after the boot is collapsed and the fluid path is created.

As described in greater detail below, the septum needle 330 can be significantly larger than the patient needles 222, such as 25-29 gauges, to allow easier handling and preventing flow restriction. As more clearly shown in FIG. 8D, the septum needle is sized to engage the septum 160 and remain buried in the septum 160. This engagement between the septum 160 and septum needle 330 creates a sterile environment through which the septum needle 330 travels when piercing the septum 160, such that at no time is the septum needle exposed to a non-sterile environment.

Returning to FIG. 2B, a bottom, or lower housing 210 is provided that can mate with the upper housing 110 and the reservoir subassembly 100 described above. The lower housing 210 can be used to trap and contain all remaining components, and can provide snap features to receive and attach components and housing members. The lower housing 210 can also include one or more guiding features for securing, releasing, and directing the button slide 320 and patient needle manifold 220 as described in greater detail below. A break line between units, such as between the upper and lower housing units, can be positioned toward vertical center of the device, which creates a more stable assembly since the push button subassembly described below can be top down loaded into a substantial housing instead of onto a plate. The upper and lower housings 110 and 210 respectively, can then be snap fit or bonded ultrasonically to one another.

The disclosed device also contains at least one patient needle 222, or microneedle, but may contain several, such as the three microneedles shown in the push button subassembly 300 of FIG. 2B. Each microneedle 222 is preferably at least 31 gauge or smaller, such as 34 gauge, and is anchored within a patient needle manifold 220 which can be placed in fluid communication with the reservoir. Each microneedle is secured to prevent disassembly from the manifold 220 at any force less than 1 pound. The microneedles 222, when more than one is included in the device, may also be of differing lengths, or gauges, or a combination of both differing lengths and gauges, and can contain one or more ports along a body length, preferably located near the tip of the needle or near the tip bevel if the needle has one.

In the embodiment described above, the use of multiple 34 gauge needles to deliver the reservoir contents is practical as the infusion occurs over a longer period than typically associated with an immediate syringe injection requiring a much larger cannula, or needle. In the disclosed embodiments, any needle can be used which targets preferably either the intradermal or subcutaneous space; however, the embodiment shown in FIG. 2B includes microneedles of between 1 and 4 mm in exposed length (i.e., 2 mm), and the arrangement of these patient needles can be in a linear or nonlinear array, and can include any number of needles as required by the specific application. Other ranges of needle lengths may be uses such as 0.5 to 1 mm. Furthermore, injections made by the device may be in any tissue space, as it is not required that injection be limited to tissue spaces discussed in the context of the specification. The mixing and reconstitution aspects of the invention could be useful in parenteral administration in general (e.g., subcutaneous, intravenous, intramuscular and intradermal delivery) or direct administration of medicaments to orifices in the body (e.g. intranasal administration). Thus, although the specific embodiments disclosed herein relate to an intradermal infusion apparatus and method, it should be noted that the invention is not to be limited to only an intradermal infusion device, as devices having aspects of the invention may be useful in devices performing parenteral administration in general.

In FIG. 2B, a push button subassembly 300 is shown and integrates a septum needle 330, septum needle manifold 322, and push button slide 320 into one piece; however, fabrication of the push button subassembly 300 may be simplified somewhat by providing a snap-on push button face plate 360 to allow for two or more simpler molded button parts. The push button slide 320 also provides a mechanism to secure the patient needle manifold in a retracted position, and release the manifold when the device is properly activated. Tubing 350 which is used to establish a fluid path as described in greater detail below exits the septum needle manifold 322 on the same side as a tubing entry to the patient needle manifold 220 allowing easier assembly and creating a flexible fluid path between the septum needle manifold and the patient needle manifold. The patient needle manifold 220 containing the patient needles 222 is assembled into tracks 324 provided by the button slide 320 and creates a stable securing and release mechanism, as described in greater detail below. Thus, septum needle 330, septum needle manifold 332, tubing 350, needle manifold 220 and needle 222 provide a selective fluid conduit between chamber 127 of reservoir 100 and the patient.

Figure 3:
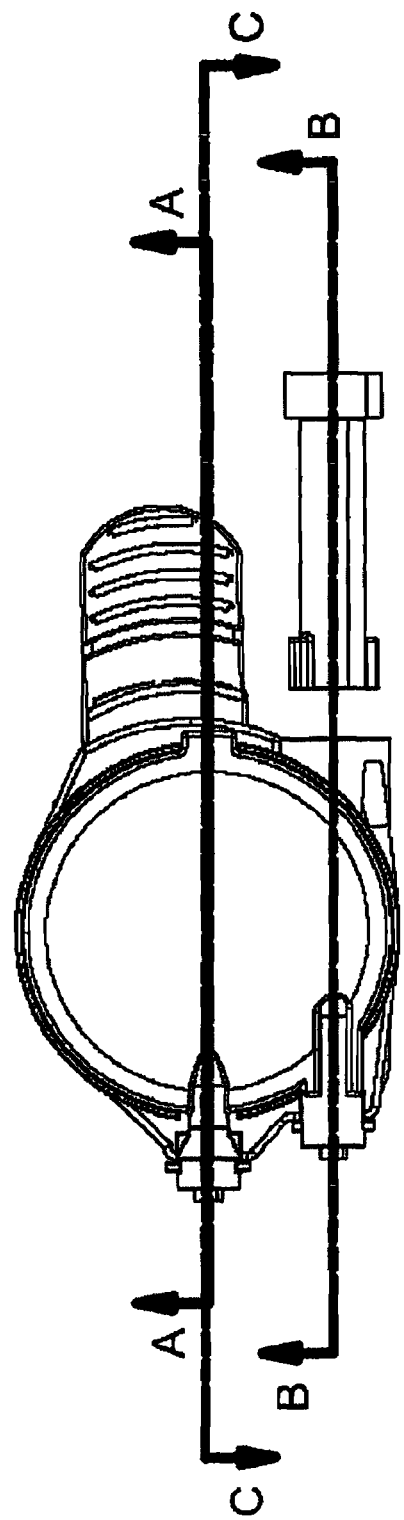
FIG. 3 is a plan view of the patch-like injector of FIG. 1A, showing axes A-A, C-C and B-B.
Figure 3A:
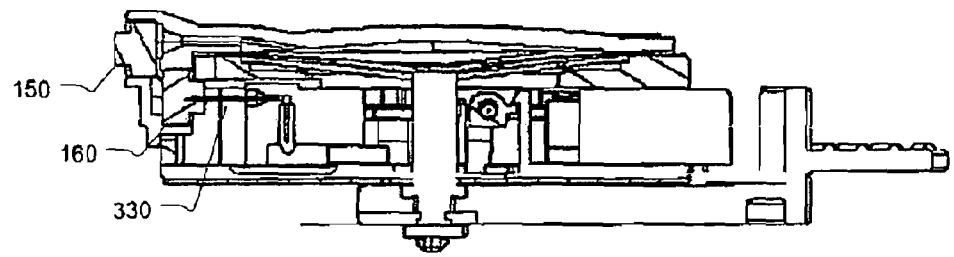
FIG. 3A is a cross-sectional side view along axis A-A of the patch like injector of FIG. 3, shown prior to insertion of the cartridge.
Figure 3B:
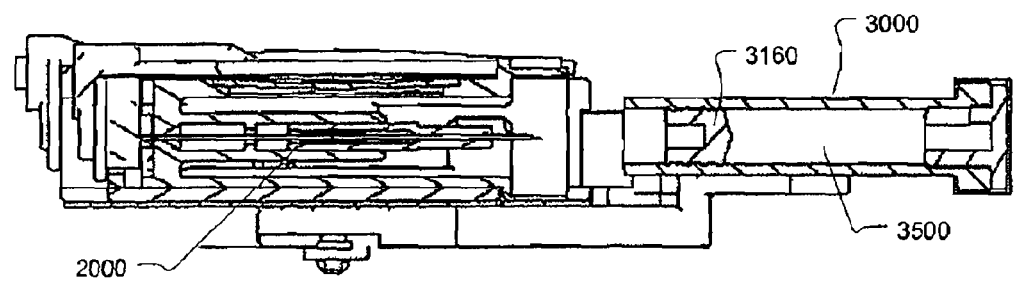
FIG. 3B is a cross-sectional side view along axis B-B of the patch like injector of FIG. 3, shown prior to insertion of the cartridge.
Figure 3C:
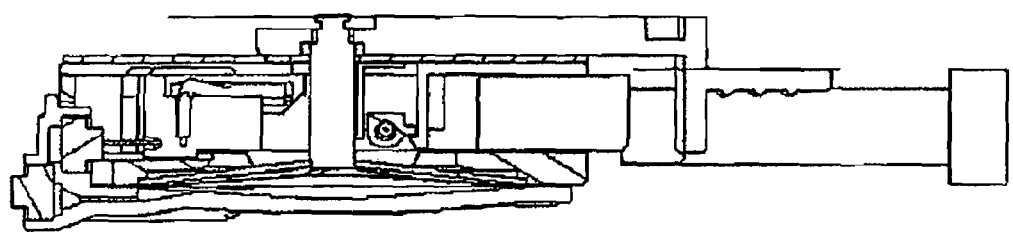
FIG. 3C is a cross-sectional side view along axis C-C of the patch like injector of FIG. 3, shown prior to insertion of the cartridge.
Figure 3D:
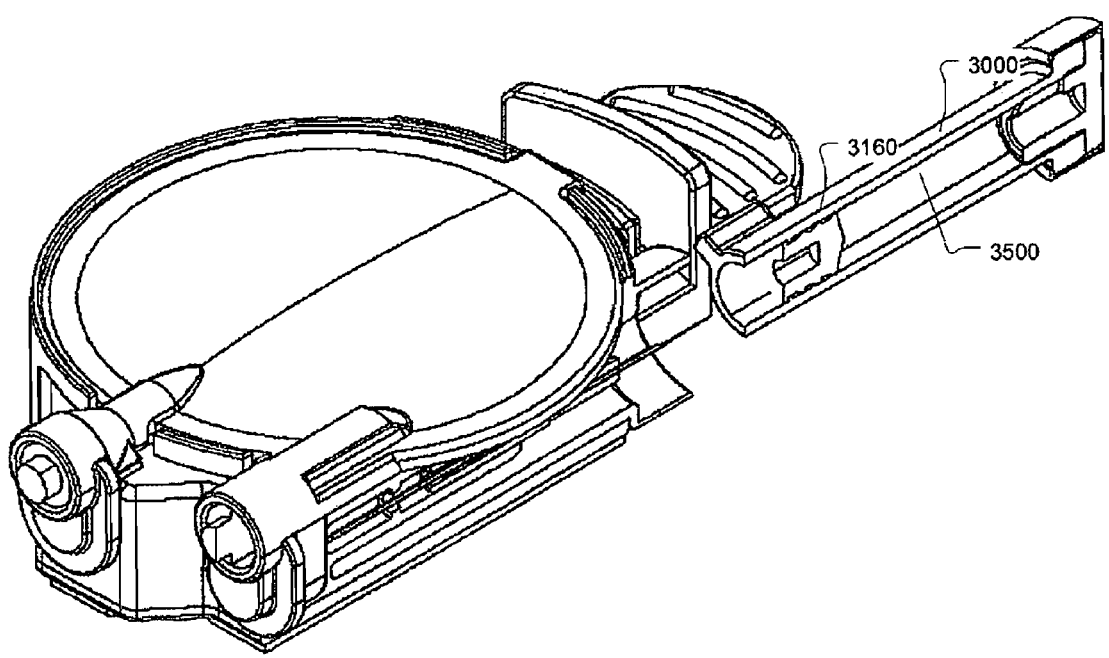
FIG. 3D is a cross-sectional top perspective view along axis B-B of the patch like injector of FIG. 3, shown prior to insertion of the cartridge.
Figure 4A:
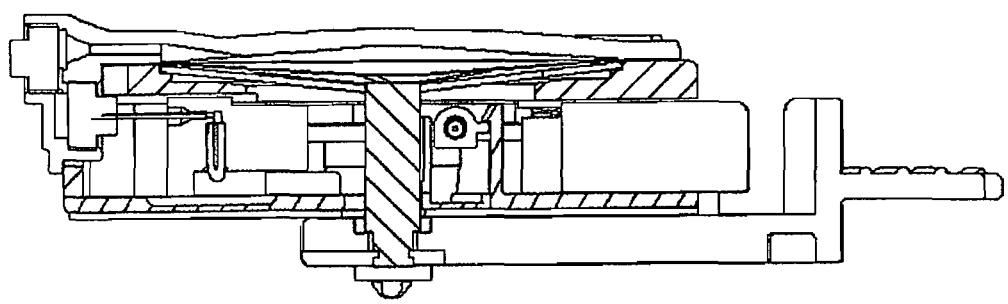
FIG. 4A is a cross-sectional side view along axis A-A of the patch like injector of FIG. 3, shown after insertion of the cartridge.
Figure 4B:
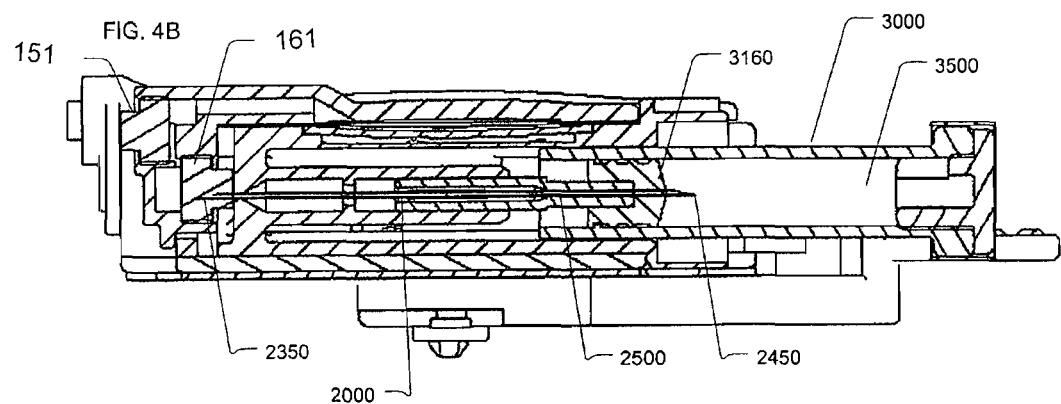
FIG. 4B is a cross-sectional side view along axis B-B of the patch like injector of FIG. 3, shown after insertion of the cartridge.
Figure 4C:
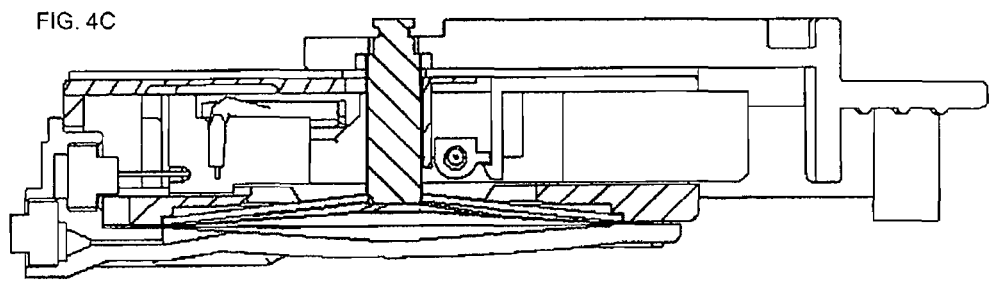
FIG. 4C is a cross-sectional side view along axis C-C of the patch like injector of FIG. 3, shown after insertion of the cartridge.
Figure 4D:
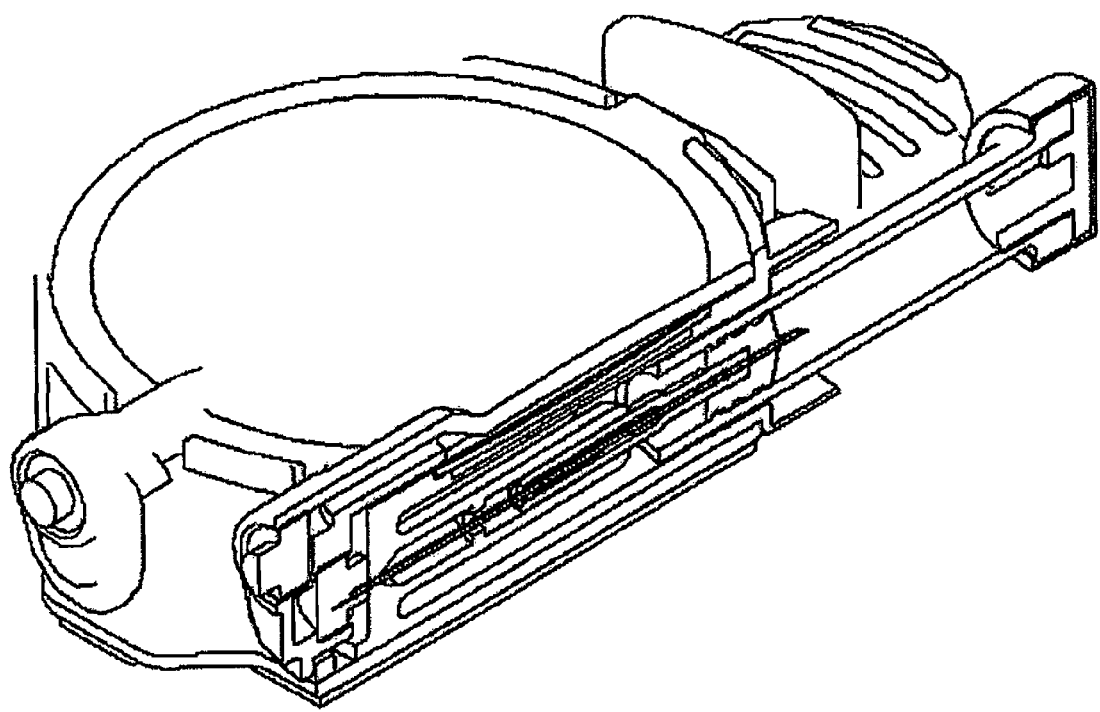
FIG. 4D is a cross-sectional top perspective view along axis B-B of the patch like injector of FIG. 3, shown after insertion of the cartridge.
Figure 5A:
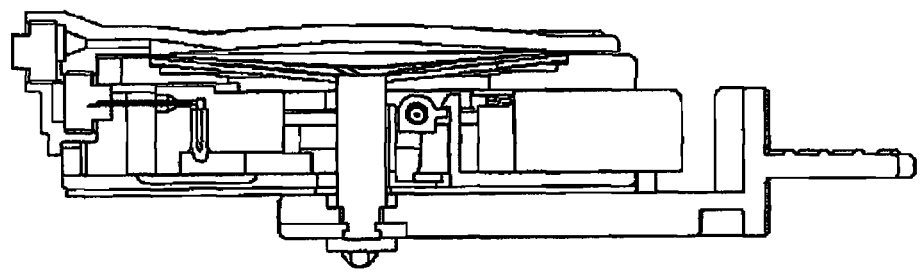
FIG. 5A is a cross-sectional side view along axis A-A of the patch like injector of FIG. 3, shown after access to the reservoir.
Figure 5B:
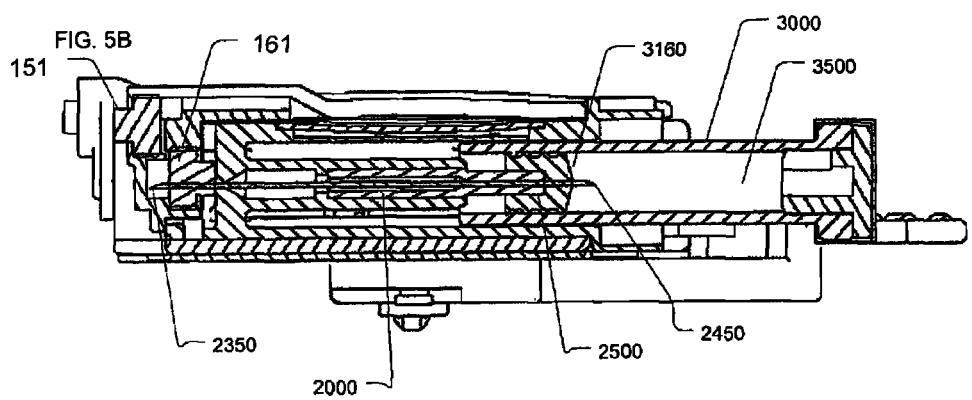
FIG. 5B is a cross-sectional side view along axis B-B of the patch like injector of FIG. 3, shown after access to the reservoir.
Figure 5C:
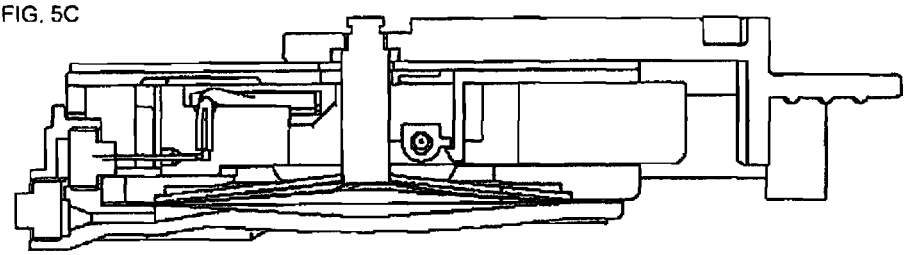
FIG. 5C is a cross-sectional side view along axis C-C of the patch like injector of FIG. 3, shown after access to the reservoir.
Figure 5D:
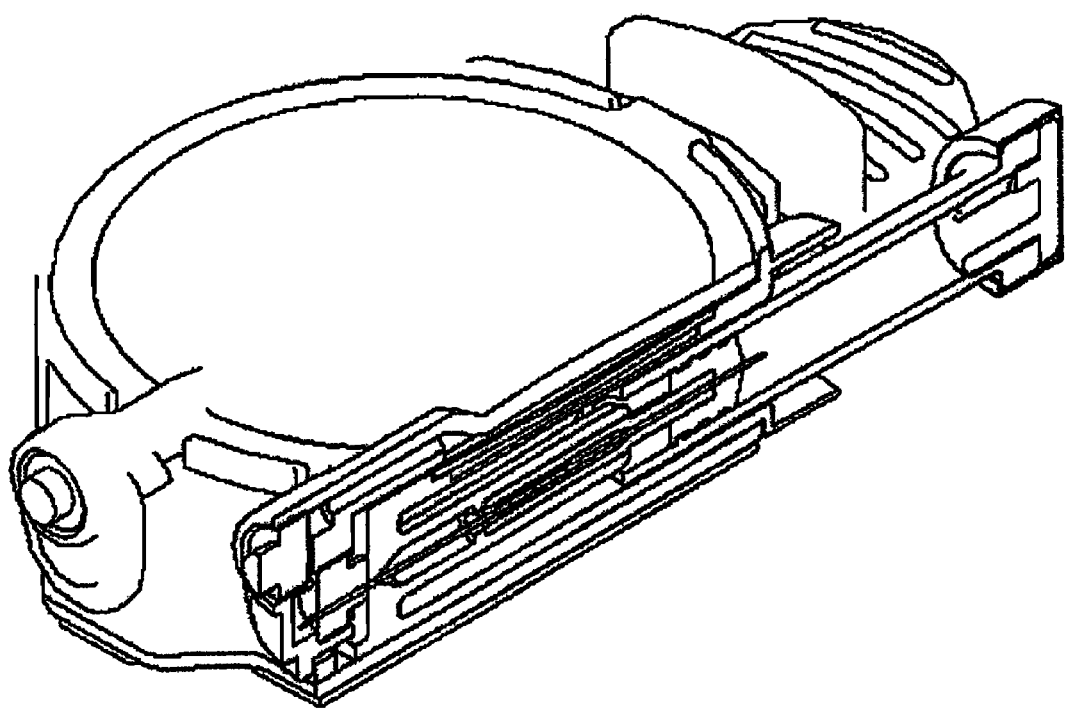
FIG. 5D is a cross-sectional top perspective view along axis B-B of the patch like injector of FIG. 3, shown after access to the reservoir.
Figure 6A:
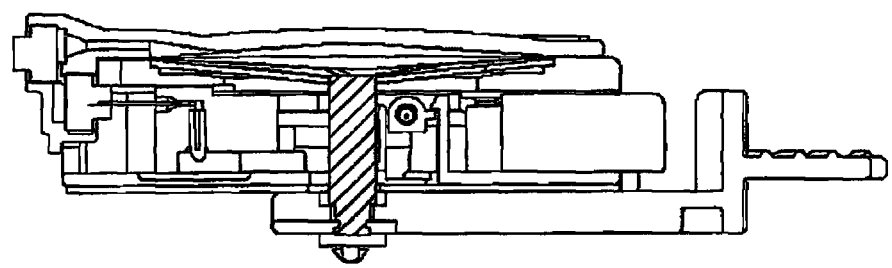
FIG. 6A is a cross-sectional side view along axis A-A of the patch like injector of FIG. 3, shown after transfer of the fluid.
Figure 6B:
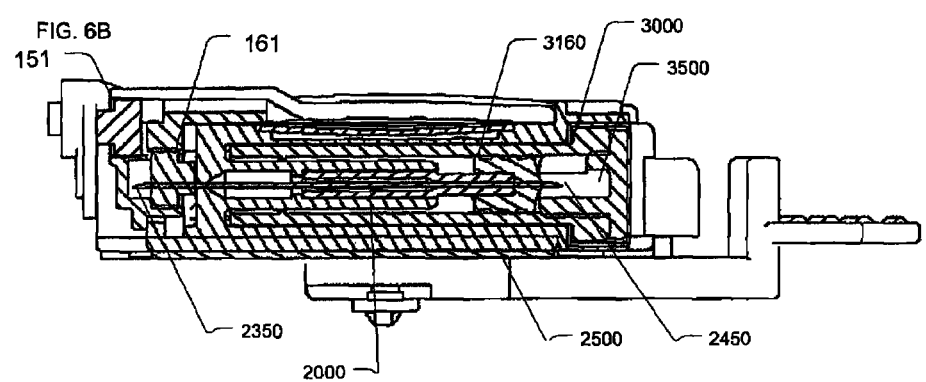
FIG. 6B is a cross-sectional side view along axis B-B of the patch like injector of FIG. 3, shown after transfer of the fluid.
Figure 6C:
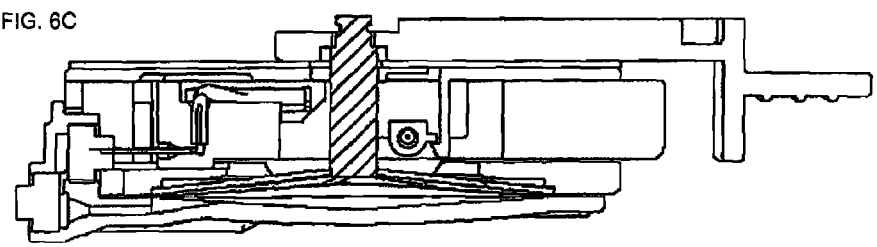
FIG. 6C is a cross-sectional side view along axis C-C of the patch like injector of FIG. 3, shown after transfer of the fluid.
Figure 6D:
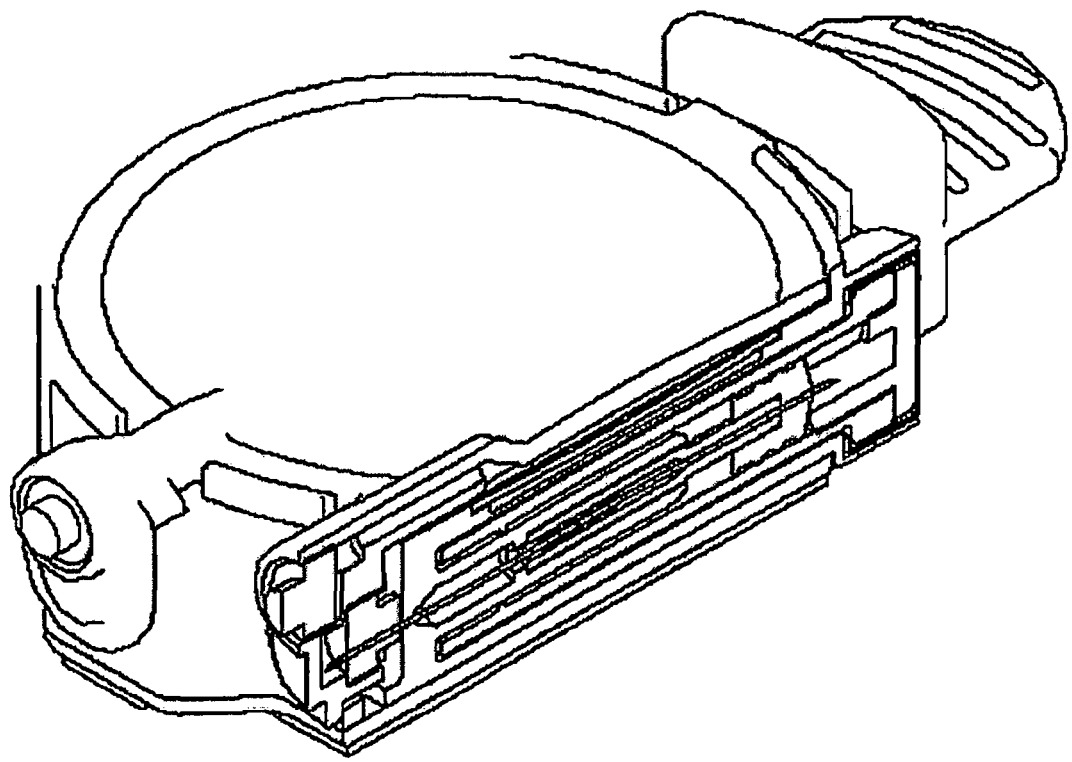
FIG. 6D is a cross-sectional top perspective view along axis B-B of the patch like injector of FIG. 3, shown after transfer of the fluid.

A top view of the first embodiment shown in FIG. 3 that illustrates the alignment and travel between the push button slide 320 and the device, which is required for activation. FIG. 3A is a side elevational view of the first embodiment and illustrates the low profile of the device and the centered positioning of the patient needle opening, which is more clearly illustrated in the bottom view of the first embodiment shown in FIG. 1B. FIGS. 3A through 8D, illustrate a number of cross-sectional views (A-A, B-B, and C-C in FIG. 3) of the present embodiment and illustrate the construction, positioning and operation of each subassembly in a pre-mixed (FIGS. 3A-3D), mixing (FIGS. 4A-4D), mixing (FIGS. 5A-5D), filled (FIGS. 6A-6D), energized (FIGS. 7A-7D), and post activated position (FIGS. 8A-8D), each described in greater detail in separate sections below.

As shown in FIG. 3A-3D, the infuser device is in a pre mixed state. The cartridge is outside of the housing and the chambers of the both the reservoir and the cartridges are sealed. Cartridge 3000 is aligned for insertion into housing 110 to begin the mixing of the medicament constituents.

As shown in FIGS. 4A to 4D, which is the first portion of the mixing step. Cartridge 3000 is at least partially inserted into housing 110 such that hub 2500 of access needle 2000 is abutting stopper 3160 and stopper end 2450 of access needle has entered chamber 3500 of cartridge 3000 such that communication between chamber 3500 and the interior of access needle 2000 is enabled. As hub 2500 is abutting stopper 3160, any further insertion of cartridge 3000 into housing 110 will cause septum end 2350 of access needle 2000 to penetrate septum 161, since access needle 2000 is slidably engaged to housing 110.

As shown in FIGS. 5A to 5D, which is the second portion of the mixing step which shows Cartridge 3000 inserted into housing 110 slightly further than in FIGS. 4A-4D. Consequently, hub 2500 has been pushed by stopper 3160 such that septum end 2350 of access needle 2000 has breached septum 161. A fluid path between chamber 3500, access needle 2000, and chamber 127 of reservoir 100 is established; thereby fluid communication between chamber 3500 and the chamber 127 of reservoir 100 is now enabled, allowing mixing of medicament constituents. Preferably, to draw medicament constituents from chamber 127, into chamber 3500, chamber 3500 has a pre-selected lower pressure with respect to chamber 127. Alternatively, the pressures in chamber 127 and chamber 3500 may be substantially equal and a fluid flow is established by manipulation of cartridge 3000 to draw constituents into chamber 3500. Alternatively, the pressures in chamber 127 and chamber 3500 may be substantially equal and substantially no fluid flow occurs and mixing occurs substantially as shown in FIG. 6A-6D.

As shown in FIGS. 6A to 6D, the contents of chamber 3500 have been substantially injected into chamber 127 of reservoir 100 by the further insertion of cartridge 3000 into housing 110. The further insertion of cartridge 3000 into housing 110 has caused translation of stopper 3160 within cartridge 3000 to reduce the volume of chamber 3500. As the stopper translates within cartridge 3000, the volume of chamber 3500 is reduced until it reaches a pre-determined dead volume. Preferably, the dead volume of chamber 3500 is minimized. As shown, the medicament mixture is substantially contained within chamber 127 of reservoir 100. At this point the medicament mixture may be viewed by the patient through the clear portions of the reservoir for proper mixture characteristics. Further aspects of the invention described herein provide for optimization of these characteristics.

Figure 7A:
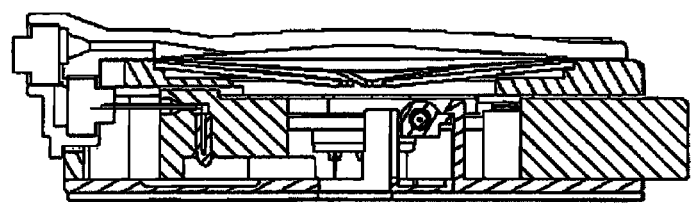
FIG. 7A is a cross-sectional side view along axis A-A of the patch like injector of FIG. 3, shown after pressurization of the reservoir.
Figure 7B:
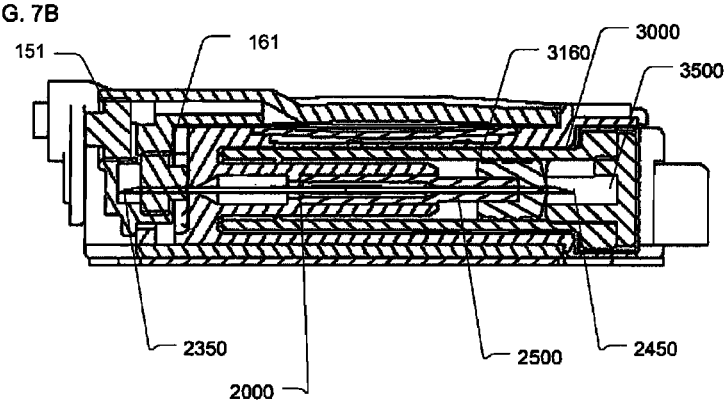
FIG. 7B is a cross-sectional side view along axis B-B of the patch like injector of FIG. 3, shown after pressurization of the reservoir.
Figure 7C:
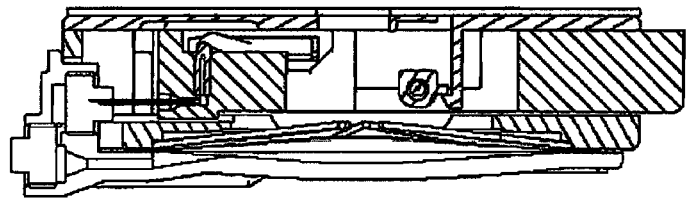
FIG. 7C is a cross-sectional side view along axis C-C of the patch like injector of FIG. 3, shown after pressurization of the reservoir.
Figure 7D:
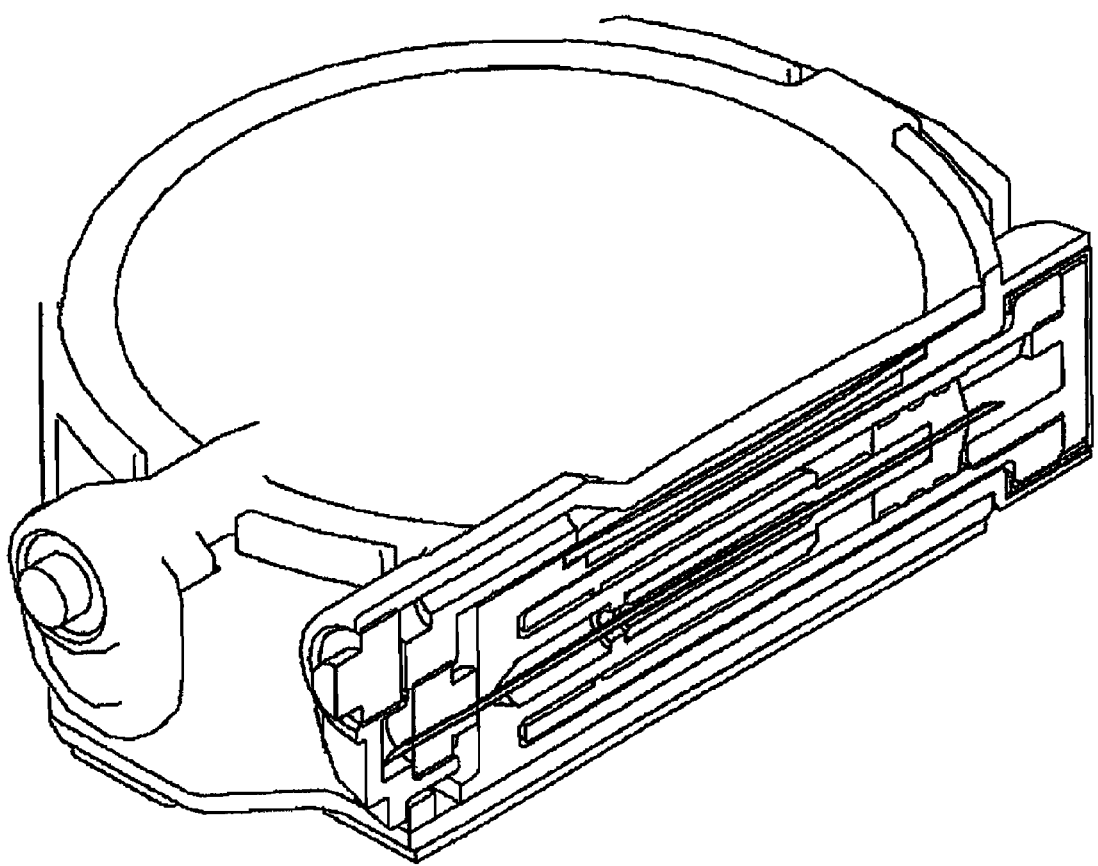
FIG. 7D is a cross-sectional top perspective view along axis B-B of the patch like injector of FIG. 3, shown after pressurization of the reservoir.

As shown in FIG. 7A-7C, which demonstrates the pressurized state, in which an exemplary pressurization system in the form of a Disk spring 130 is included in the device 1000 for applying an essentially even, constant force to the reservoir to force the contents from the reservoir, and is hereinafter sometimes referred to as a "constant force spring". The constant force spring 130 is used to store energy that, when released by device activation, pressurizes the reservoir at the time of use. The spring 130 is held in a flexed state by a pin 140 positioned at the center of a plurality of spring fingers. In doing so, the spring is prevented from putting stress on the film 170 of the reservoir subassembly 100 or any remaining device components during storage and reconstitution.

The pin 140, or retaining pin, can be any suitable pin, tube or ring, that is sufficiently rigid to resist spring tension and deformation, and secure the pin to a removal mechanism, such as a pull handle 260 described in greater detail below. The pin 140 should not fail under normal tensile load or, if part of an assembly, should not disassemble at forces that can be induced by shipping and handling, and resulting in inadvertent activation. Pull handle 260 is provided to aid in the removal of the retaining pin 140 described above. The pull handle 260 is positioned adjacent to the bottom surface of the device, and includes one or more members, which extend to one side of the device creating a mechanical advantage for the removal of the retaining pin 140. In the embodiment shown, the pull handle 260 includes a member 262 that extends and shields the button head 360 of the push button subassembly 300. In doing so, the pull handle 260 prevents the application of a force to the push button 360 until the pull handle is removed. This prevents accidental activation of the device via the push button prior to proper placement. Optionally, the pull handle 260 includes a member, which prevents the application of a force to the push button. In other versions of this embodiment, the pull handle can include a member that extends between the push button and the device housing to prevent movement of the push button when a force is applied to the push button.

When the retaining pin 140 is pulled free of the Disk spring 130, the fingers of the spring are released and free to bias towards the film, and in doing so, exert a force on the film lid 170 of the reservoir subassembly 100. The edge of the spring 130 is trapped between the reservoir and the upper housing, and can be configured to preferably create a pressure within the reservoir of from about 1 to 50 psi, and more preferably from about 2 to about 25 psi, and most preferably from about 15 to about 20 psi for intradermal delivery of the reservoir contents. For sub-cutaneous injection or infusion, a range of about 2 to 5 psi may be sufficient. The Disk spring can be sized between about 1.15 to 1.50 inches in diameter, preferably 1.26 inches, to allow for a full 750 microliter delivery. A Belleville washer, or disk spring, exhibits a load characteristic, shown as a percentage of flat position load deflection, as the spring travels from a flat or flexed state to a relaxed state. One skilled in the art may select a spring size and rate to deliver a range of volumes.

Figure 8A:
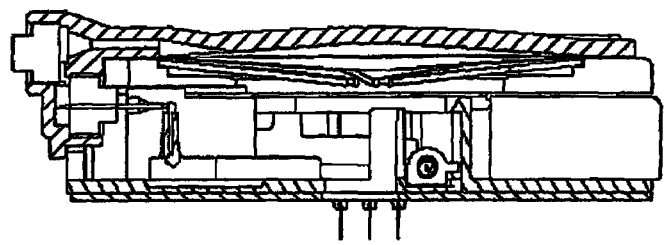
FIG. 8A is a cross-sectional side view along axis A-A of the patch like injector of FIG. 3, shown after deployment of the needle.
Figure 8B:
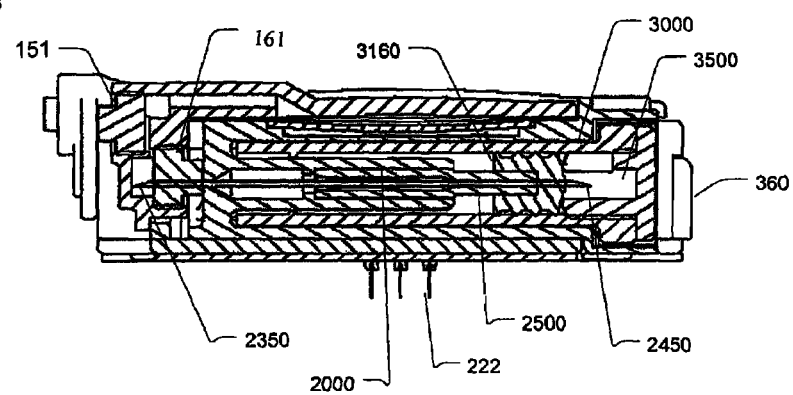
FIG. 8B is a cross-sectional side view along axis B-B of the patch like injector of FIG. 3, shown after deployment of the needle.
Figure 8C:
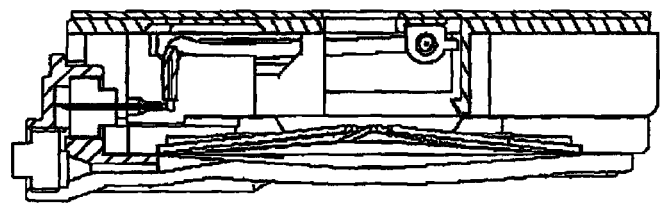
FIG. 8C is a cross-sectional side view along axis C-C of the patch like injector of FIG. 3, shown after deployment of the needle.
Figure 8D:
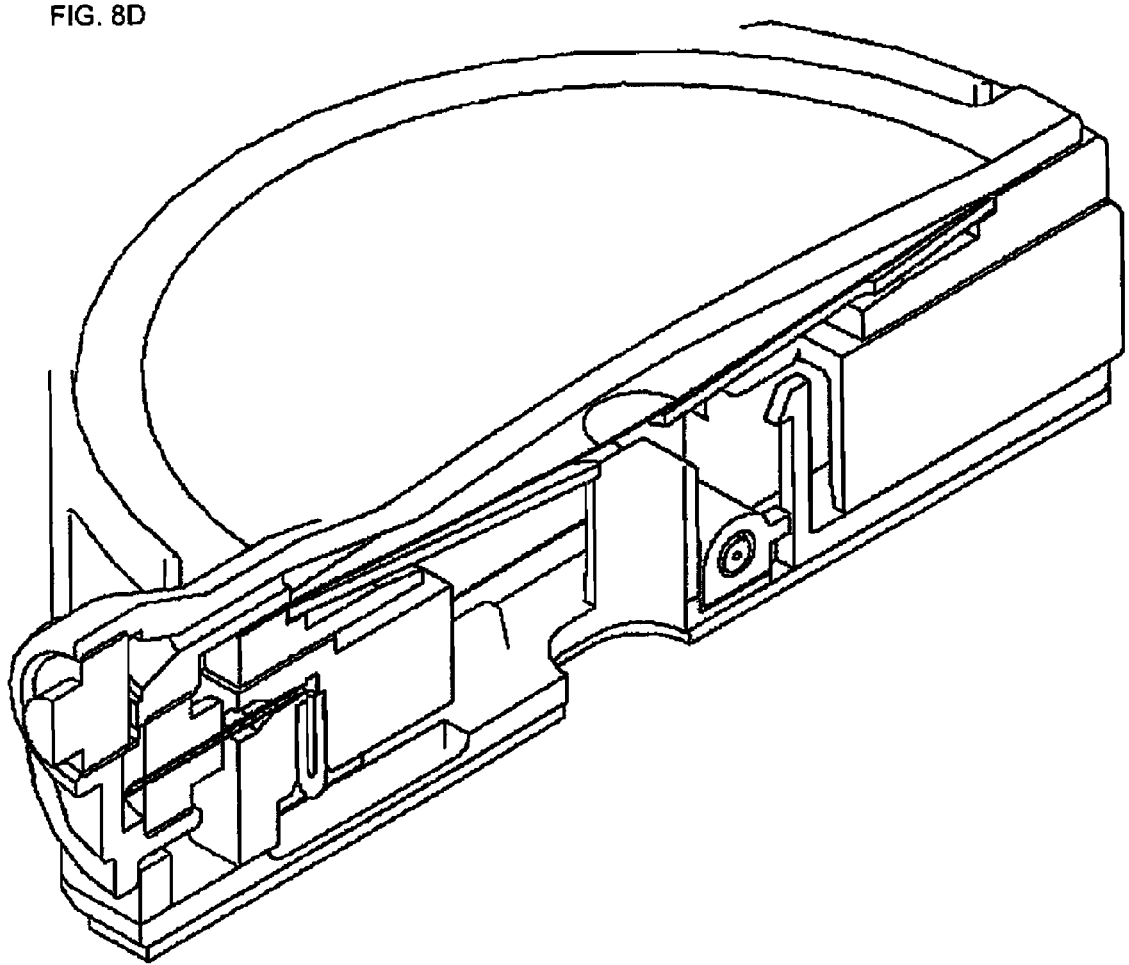
FIG. 8D is a cross-sectional top perspective view along axis B-B of the patch like injector of FIG. 3, shown after deployment of the needle.

As shown in FIGS. 7A to 7D, a disk spring 130 is provided to apply a substantially even and constant pressure to the flexible film 170 of the reservoir subassembly 100, compressing the contents of the reservoir between the flexible film 170 and the rigid portion 120, and forcing the contents from the reservoir through one or more flow paths as shown in greater detail in FIG. 8D, which illustrates a partial cross-sectional view of the fluid path and reservoir. As noted above, the reservoir of FIG. 1A can also be made up of two or more flexible, non-distensible films, wherein the contents can be contained between the films where at least one film is attached to the rigid portion 120 to provide a rigid base for compressing and pressurizing the contents of the reservoir. In yet another embodiment of the reservoir subassembly 100, the flow rate is automatically adjusted from an initial high rate to one or more stepped-down lower flow rates. Additional details of an adjusting flow rate are further discussed in U.S. patent application Ser. No. 10/396,719, entitled "Multi-Stage Fluid Delivery Device and Method", filed on Mar. 26, 2003, the entire content of which is incorporated herein by reference.

As shown in FIG. 8A-8D an activated position is provided, or in-use position. As the patient needle manifold 220 remains stationary relative to the slidable movement of the button slide 320, the activated position is provided as the button slide is slidably engaged and detented in this position. In the activated position, the septum 160 is penetrated, and the manifold is released and forced downward towards the user's skin surface, driven by the spring 310. In the embodiment shown, the force required to penetrate the septum 160, move the needle within the septum and release the patient needle manifold 220, in moving to this activated position is typically between 2 and 4 pounds.

The patient needle and septum needle manifold assemblies 220 and 322 respectively, enable access and discharge of fluid contained within the reservoir and delivery of the fluid to the patient needles 222. Each manifold housing therefore contains a number of fluid flow paths for routing reservoir contents received from the septum needle 330, or other protuberance, and any associated tubing or conduits 350, and delivering the contents to the patient needles 222 and into the skin of the user. The patient needle manifold 220 in which the patient needles 222 are anchored is in fluid communication with the septum needle manifold 322, in which the septum needle 330 is anchored, by way of a flexible tubing 350. Alternatively, tubing 350 could be a conduit formed by the fluid-tight assembly of two or more components.

The patient needle manifold 220 is held in a pre-release, or "up" state, under load, provided by one or more springs 310, by the push button subassembly 300 and lower housing 210. In the first version of securing the patient needle manifold 220 in an up state described above, the patient needle manifold 220 slidably engages a set of tracks 324 disposed on the button slide 320. As the patient needle manifold 220 remains stationary within a chute 212 provided by the lower housing 210, the button slide 320 slidably travels until a track opening 325 aligns with the patient needle manifold 220, releasing the patient needle manifold 220 from the tracks 324 within the chute.

In each version described above, one or more drive springs 310 exert a force on the top of the patient needle manifold 220 to drive the manifold when activated, or released from the up state, allowing for patient needle 222 seating when the manifold is released, and creating a fluid path between the septum needle, septum needle manifold, flexible tubing, patient needle manifold and the array of patient needles. The drive springs 310 serve to "plant" the needles into the skin via the spring-loaded patient needle manifold 220 which can travel at a speed ranging between 15 and 26 miles per hour (between 6 and 12 meters per second)

The slidable motion of the button slide 320 also pushes the septum needle 330 through the septum 160, creating a flow path between the reservoir and the septum needle. A septum needle containing manifold 322 can be attached or constructed as a component of the button slide 320, and moves with the button slide during activation steps until the septum needle 330 penetrates the septum boot 340, and subsequently the septum 160. Depending upon the sequence desired, prior to, concurrent with, or slightly after the septum needle 330 penetrates the septum 160, the patient needle manifold 220 is released and bottoms out against the skin surface, seating the patient needles 222 and thereby initiating flow of energized fluid from the reservoir, through the septum needle and septum needle manifold, through the flexible tubing attached to the septum needle manifold, and to the patient needles of the patient needle manifold.

One or more septum needles 330 can be provided, separate from the patient microneedles 222, allowing greater flow within the complete fluid path between reservoir and patient needles. In the embodiment described above, the complete fluid path includes in part, two or more needles, specifically, at least one septum needle 330, and at least one patient microneedle 222. This allows the device to incorporate needles of different constructions depending upon the fluid path characteristics desired. For example, the patient microneedles 222 can include one or more 34 gauge needles, where the septum needle 330 can include one or more equal or larger needles as required. Additionally, the separation of the patient and septum needles allows further freedom of movement of the patient needles during operation of the device. Furthermore, one or more reservoirs may be employed in the device, allowing greater or altered flow characteristics within the complete fluid path between reservoir and patient needles.

A flexible tube 350 can be used to connect the septum needle 330 and/or septum needle manifold 322 to the patient needle manifold 220. The flexible nature of the tube coupling allows the patient needle manifold 220 to move with greater independence from the remaining components of the device, allowing more effective needle seating. As such, the term "tubing" 350 encompasses any conduit which may be formed by the fluid-tight assembly of two or more components and allows flow between the desired manifolds. Once properly seated, the patient needle manifold 220 completes the fluid path between the flexible tubing 350 and the array of patient microneedles 222, and the user's skin. As noted above, the patient needle manifold 220 is guided into position by features in the lower housing 210, and the drive springs 310 described above exert a force on top of the patient needle manifold 220 allowing for needle seating when the manifold is released. A variety of drive spring options exist, including the use of as few as one or as many as four coil springs, or one or more leaf springs.

The subassembly embodiments presented above are not restrictive, and can be reconfigured as required in a given application. The embodiment of aspects of the present invention described above is a push-button design wherein the device is first energized, then positioned and affixed to a skin surface, and activated by gently pressing a slide button as shown in FIGS. 7A through 8D. Specifically, the user first removes the device from a sterile packaging and energizes the system prior to adhering the device to the skin by removing the pull handle 260 from the bottom surface of the device as shown in FIGS. 7A-&C, in a motion similar to opening a soda can or peeling open an orange. The pull handle 260 is positioned and extends to one side of the device thereby creating a mechanical advantage for the removal of the pull handle and attached retaining pin 140, which can be removed with no more than a reasonable amount of force that can be exerted by a wide range of users (i.e. typically less than 3 pounds). As shown in FIG. 7A, the removal of the pull handle 260 removes the retaining pin 140, and can also simultaneously remove an adhesive cover (not shown) and/or a needle cap 240, as described in greater detail below. In yet another version of this embodiment, the pull handle 260 can be incorporated with the product packaging, such that when the package is opened and the device is removed, the retaining pin 140, adhesive cover and/or the needle cap 240 is also removed.

Upon removal of the device from the package and prior to use, the features described above allows the user to then inspect both the device and the contents therein, including inspection for missing or damaged components, expiration dates(s), hazy or color-shifted drugs, and so forth. After use, the user can once again inspect the device to ensure the entire dose was delivered. In this regard, the device can include an administered dose indicator for example, a readable gauge area that is at least 20% of the surface area of the device housing and accurate to within +/−10% of the labeled dose. Both cartridge 3000 and reservoir 100 may be inspected in this manner.

After inspection, cartridge 3000 is inserted into housing 110 which allows the low pressure of chamber 3500 in cartridge 3000 to draw the medicament from chamber 127 of reservoir 100 into cartridge 3000. Upon mixture of medicament constituents in cartridge 3000 with medicament constituents formally in reservoir 100, cartridge 3000 is inserted further into housing 110, which moves stopper 3160 within cartridge 3000 and expels the mixture from cartage 3000 back into reservoir 100. As the mixture is ready for injection it may be further inspected via observation through clear portions of reservoir 100. Once the inspection is complete the user may pull retaining pin 140, thereby pressurizing reservoir 100. Once pin 140 has been pulled a sufficient distance from the device to disengage from the spring, the fingers of the Disk spring 130 are released and are free to drop against the reservoir film 170 within the device. The activation button 360 and button slide 320 of the button subassembly 300 can be either interlocked with, and/or shielded by the pull handle 260, such that the activation button 360 cannot be pushed until the pull handle 260 has been removed, thus preventing inadvertent activation or incorrect order of operation by the user. Once removal of the pull handle 260, retaining pin 140, adhesive cover and needle cap 240 is accomplished as shown in FIG. 7A, the device is energized and ready for positioning and activation. This energizing step releases the Disk spring 130 allowing it to press against the flexible film 170 of the reservoir subassembly 100, pressurizing the reservoir and the substance communication path up to the septum 160, and prepares the device for activation.

After pressurization, the device is positioned and applied to the user's skin surface. Like a patch, the user firmly presses the device onto the skin and the lower housing 210 includes a bottom surface that allows for the adhesive layer 250 to secure the device to the skin of the user. This bottom surface of the lower housing 210 can be flat, contoured, or shaped in any suitable fashion, and includes an adhesive layer 250 thereon, which would most likely be covered prior to shipping. Prior to use, the user peels back the adhesive covering, such as a film covering the adhesive, thereby exposing the adhesive for placement against the skin. The adhesive should preferably adhere to the bottom surface of the device with a peel force of not less than 2 pounds, and include a covering that should preferably release from the adhesive with a peel force of less than ½ pound. Once removed, the user is then able to place the device against the skin and press to ensure proper adhesion (i.e. application of a vertical load of 3 pounds). In versions of the embodiment in which a removable needle cover 240 is provided, the needle cover should preferably remove from the device with a force not to exceed 2 pounds.

Once properly positioned, the device is activated by sliding the button 360 and attached button slide 320 of the push button subassembly 300 towards the center of the device as shown in FIG. 8A. With no more than a reasonable amount of force applied by the user (i.e. between 2 and 4 pounds), the activation button can be depressed completely to allow activation. The button and button slide extends within the device and includes at least one slot which, in a non-release position, holds the patient needle manifold 220 up against the compressive force of one or more driving springs 310.

As the user pushes the button, the first event to occur is the button pushing the septum needle 330 through the septum 160, creating a flow path between the reservoir and the patient needles. As noted above, the "shipping" position has already brought the septum needle and septum into contact. Further motion of the button then releases the patient needle manifold 220 as described above, allowing the patient needles 222 to seat into the skin of the patient driven by the force of one or more driving springs 310. At this point, the button 360 and button slide 320 locks into place giving a positive audible and tactile feedback to the user indicating that infusion has begun.

The button subassembly 300 sequence of operation described above can be varied in other embodiments of the same or similar device. In one such embodiment for example, as the button is pushed by the user, the first event to occur is the patient needle manifold 220 releasing and allowing the patient needles 222 to seat into the skin of the patient driven by the force of the driving springs 310. Further motion of the button then pushes the septum needle 330 through the septum needle boot 340 and septum 160 to create a fluid path. Either method can be implemented, but failure modes of each can be different. For example, in an operation sequence in which flow is initiated before the patient needle manifold is released, if the patient needles fail to seat properly a wet injection will typically occur.

The flexible tubing 350 in each embodiment connects the septum needle 330 or septum needle manifold 322 now in fluid communication with the reservoir, to the patient needle manifold 220 now in fluid communication with the user, and is sufficiently flexible to allow the patient needle manifold to move independently of any other device component. In addition, as with the tortuous path established by the patient needle manifold channels described above, the tubing 350 can also serve as a flow restriction where required.

Once activated, the user typically leaves the device in position, or "wears" the device, for some period of time, such as five minutes to seventy-two hours for complete delivery of the device contents, and then removes and discards the device with no damage to the underlying tissue. However, upon intentional or accidental removal, one or more safety features can deploy as described in greater detail below to shield the exposed needles resulting from activation. The safety features however can be configured to not deploy if the button and button slide has not been pushed and the patient needles extended.

In addition to the performance advantages described above, another advantage of the embodiment of FIG. 1 described above is the ability to make two or more distinct, self-contained subassemblies that allow for assembly flexibility. Each subassembly is self-contained and stable, and provides the ability to separate the reservoir assembly from remaining components, allowing separate filling and inspection of the reservoir, while preventing the unnecessary handling of the remaining components. Additionally, should any of the additional components be discarded, the costly reservoir contents can be retained and used in another assembly. Also, the reservoir contains no unnecessary parts and as a result, brings a low particle load into filling operations. Also, all stored energy components are in the body subassembly so they cannot be inadvertently deployed during filling of the reservoir. Specifically, no springs are included in the reservoir, which prevents the chance of unwanted spring release during filling. As noted, minimal extraneous components in the reservoir reduce particle load, and only contains necessary components, such as the reservoir, lid, septum and stopper. No dangling parts are present, and remaining parts for remaining subassemblies typically require only drop-in assembly steps.

A further advantage of the embodiment of FIG. 1 described above includes the location of patient needles near the center of the device footprint. Such placement reduces the effects of needle displacement due to device movement, such as "rocking". The patient needle manifold is constructed having a low mass, due in part to providing a separate manifold for the septum, thus providing a higher patient needle manifold velocity during activation. The patient needle manifold is provided with independent direct drive of patient needles, as the drive springs are located directly over the patient manifold, and serve to drive the patient needle manifold exclusively. The septum penetration force and boot collapse force have no influence on patient needle manifold movement. Additionally, there is room to include larger needle spacing and a lower activation force is sufficient, however, inadvertent activation due to such lower forces is prevented by numerous activation lockouts.

Sufficient room is also provided for a traditional septum, as well as sufficient room allowing the use of flexible tubing, or any number of flow restrictors, such as capillary tubes, for flow restriction. This can be provided while still maintaining a smaller device footprint. Additionally, the reservoir can be located on top of the device, which can allow full and unobscured view of the drug reservoir through a transparent component, allowing view of the reservoir contents to the user or manufacturer.

In each embodiment described above, the reservoir subassembly of the infusion device can be comprised of a rigid portion used in conjunction with one or more non-distensible but flexible films, such as metallized films, and can contain any number of substances between either a first and second film, where either the first or second film is also positioned against the rigid portion, or between a first film and the rigid portion. The rigid portion, or reservoir base, can be comprised of and serve as a hard portion of the reservoir against which the flexible film can be pressed as described in greater detail below. The rigid portion can contain a dished out central section and a flange, provided about the perimeter of the rigid portion to allow for heat-sealing the flexible film, or film lid to the rigid portion and forming a content reservoir, or chamber, therebetween. As at least one wall of the chamber comprises a flexible film and at least one wall of the chamber comprises a rigid surface, one or more pressurization systems can be placed adjacent to the flexible film and used to apply a substantially constant pressure to the flexible film, and pressurize the reservoir chamber and contents. As noted above, the reservoir can also be made up of two or more flexible, non-distensible films, wherein the contents can be contained between the films and at least one film is attached to the rigid portion to provide a rigid base for compressing and pressurizing the contents of the reservoir. In yet another embodiment of the reservoir subassembly, the flow rate is automatically adjusted from an initial high rate to one or more stepped-down lower flow rates. Additional details of an adjusting flow rate are further discussed in a U.S. patent application of Jim Fentress et al., Ser. No. 10/396,719, filed Mar. 26, 2003, entitled "Multi-Stage Fluid Delivery Device And Method", the entire content of which is incorporated herein by reference.

The flexible film of the reservoir subassembly can be made of non-distensible materials or laminates, such as metal-coated films or other similar substances. For example, one possible flexible laminate film which can be used in the reservoir subassembly of the first embodiment can be comprised of a first polyethylene layer, a second chemical layer as known to those skilled in the art to provide an attachment mechanism for a third metal layer which is chosen based upon barrier characteristics, and followed by a fourth layer comprised of either polyester or nylon. By utilizing a metal-coated or metallized film in conjunction with a rigid portion, the barrier properties of the reservoir are improved, thereby increasing or improving the shelf life of the contents contained within. For example, where reservoir content includes insulin, the primary materials of contact in the reservoir subassembly of the embodiment described above include linear, low-density polyethylene (LLDPE), low-density polyethylene (LDPE), cyclic olefin copolymer (COC) and Teflon. As described in greater detail below, the primary materials of contact in the remaining flow path of the reservoir contents include polyethylene (PE), medical grade acrylic, and stainless steel. Such materials which are in extended contact with the contents of the reservoir subassembly preferably pass ISO 10-993 and other applicable biocompatibility testing.

The reservoir of the reservoir subassembly is further preferably able to be stored for the prescribed shelf life of the reservoir contents in applicable controlled environments without adverse effect to the contents and is capable of applications in a variety of environmental conditions. Additionally, the barrier provided by the components of the reservoir do not permit the transport of gas, liquid and solid materials into or out of the contents at a rate greater than that allowable to meet the desired shelf life. In the embodiments shown above, the reservoir subassembly materials are capable of being stored and operated in a temperature range of approximately 0 to 120 degrees F., and can have a shelf life of two or more years. Other variations of materials may be selected which allow for thermal cycles to room temperature and back to cold storage, as well as other temperature operating ranges, beyond 0 to 120 degrees F.

In addition to satisfying stability requirements, the reservoir can further ensure operation by successfully passing any number of leak tests, such as holding a 30 psi sample for 20 minutes without leaking. Additional filling, storage and delivery benefits resulting from the configuration of the reservoir subassembly include minimized headspace and adaptability as described in greater detail below.

The reservoir of the reservoir subassembly is preferably evacuated prior to filling, as described in greater detail below. By evacuating the reservoir prior to filling, and having only a slight depression in the hard floor of the rigid portion, headspace and excess waste within the reservoir can be minimized. In addition, the shape of the reservoir may be configured to adapt to the type of energizing mechanism used, e.g., a disk or Disk spring having any number of diameter and height dimensions. Additionally, using an evacuated flexible reservoir during filling minimizes any air or bubbles within the filled reservoir. The use of a flexible reservoir is also very beneficial when the device is subjected to external pressure or temperature variations, which can lead to increased internal reservoir pressures. In such case, the flexible reservoir expands and contracts with the contents, thereby preventing possible leaks due to expansion and contraction forces. Alternate filling methods may also be employed, such as described in U.S. patent application Ser. No. 10/679,271, filed on Oct. 7, 2003 the entire contents of which is incorporated herein by reference in its entirety.

Yet another feature of the reservoir subassembly includes the ability to permit automated particulate inspection at the time of fill, or by a user at the time of use. One or more reservoir barriers, such as the rigid portion, can be molded of a transparent, clear plastic material, which allows inspection of the substance contained within the reservoir. The transparent, clear plastic material is preferably a cyclic olefin copolymer that is characterized by high transparency and clarity, low extractables and biocompatibility with the substance contained in the reservoir. In such applications, the reservoir includes minimal features, which could possibly obstruct inspection (i.e. rotation during inspection is permitted).

A fluid path between the reservoir and the patient microneedles in the embodiments described above is constructed of materials similar or identical to those described above for the reservoir subassembly, and that satisfy numerous biocompatibility and storage tests. For example, as shown in Table 1 below, where a device content includes insulin, the primary materials of contact in the reservoir subassembly of the embodiments include linear, low-density polyethylene, cyclic olefin copolymer and Teflon, and can also include a transparent, clear plastic. The primary materials of contact in the remaining flow path between the reservoir subassembly and the microneedles of the patient needle manifold include polyethylene, medical grade acrylic, and/or stainless steel.

TABLE 1

| Path Component | Material |
| --- | --- |
| Reservoir | Polyethylene, cyclic olefin copolymer and/or Teflon |
| Reservoir Film | metal-coated film, such as polyethylene, aluminum, polyester and/or nylon with a chemical tie layer, such as the product such as the product A83, manufactured by Beacon Converters of Saddle Brook N.J. |
| Cartridge | Glass or Plastic (same as reservoir) or combination thereof. |
| Cartridge Stopper | Elastomer |
| Patient Needle Manifold | Polyethylene and/or medical grade acrylic |
| Patient Needle | Stainless steel |
| Access Needle | Stainless Steel |

Specifically, the patient needles can be constructed of stainless steel, and patient needle manifold can be constructed of polyethylene and/or medical grade acrylic. Such materials when in extended contact with the contents of the reservoir subassembly preferably pass ISO 10-993 biocompatibility testing.

As shown in each embodiment above, a disk or Disk spring is included in the device for applying an essentially even, constant force to the reservoir to force the contents from the reservoir, and is hereinafter sometimes referred to as a constant force spring. The constant force spring is used to store energy that, when released by device energizing, pressurizes the reservoir at the time of use. The spring is held in a flexed state by a retention disk, or handle, that is positioned at the center of a plurality of spring fingers. In doing so, the spring is prevented from putting stress on the film of the reservoir subassembly or any remaining device components during storage. The retaining disk is sufficiently rigid to resist spring tension and deformation, and should not fail under normal tensile load.

Each embodiment described above also contains at least one patient needle, or microneedle, but may contain several, such as the three microneedles. Each microneedle is preferably at least 31 gauge or smaller, such as 34 gauge, and is anchored within a patient needle manifold which can be placed in fluid communication with the reservoir. The microneedles, when more than one is included in the device, may also be of differing lengths, or gauges, or a combination of both differing lengths and gauges, and can contain one or more ports along a body length, preferably located near the tip of the needle or near the tip bevel if the needle has one.

In the embodiments described above, the use of multiple 34 gauge needles to deliver the reservoir contents is practical as the infusion occurs over a longer period than typically associated with an immediate syringe injection requiring a much larger cannula, or needle. In the disclosed embodiments, any microneedles can be used which target either an intradermal or subcutaneous space, however, the embodiments shown above include intradermal microneedles of between 0.5 and 4 mm in length (i.e., 2 mm), and the arrangement of these patient needles can be in a linear or nonlinear array, and can include any number of needles as required by the specific application. Alternatively, other lengths and gages may be used for parenteral delivery to other tissue spaces.

The patient needles are positioned in a patient needle manifold. In the patient needle manifold of each embodiment described above, at least one fluid communication path, or feed channel, is provided to each patient needle. The manifold may simply have a single path to one or more patient needles, or may provide multiple fluid paths or channels routing contents to each needle separately. These paths or channels may further comprise a tortuous path for the contents to travel, thereby affecting fluid pressures and rates of delivery, and acting as a flow restrictor. The channels or paths within the patient needle manifold can range in width, depth and configuration depending upon application, where channel widths are typically between about 0.015 and 0.04 inch, preferably 0.02 inch, and are constructed to minimize dead space within the manifold.

The devices and methods described herein are suitable for use in administering various substances, including medications and pharmaceutical agents, to a patient, and particularly to a human patient. As used herein, a pharmaceutical agent includes a substance having biological activity that can be delivered through the body membranes and surfaces, and particularly the skin. Examples, listed in greater detail below, include antibiotics, antiviral agents, analgesics, anesthetics, anorexics, antiarthritics, antidepressants, antihistamines, anti-inflammatory agents, antineoplastic agents, vaccines, including DNA vaccines, and the like. Other substances that can be delivered intradermally or subcutaneously to a patient include human growth hormone, insulin, proteins, peptides and fragments thereof The proteins and peptides can be naturally occurring, synthesized or recombinantly produced. Additionally, the device can be used in cell therapy, as during intradermal infusion of dendritic cells. Still other substances which can be delivered in accordance with the method of the present invention can be selected from the group consisting of drugs, vaccines and the like used in the prevention, diagnosis, alleviation, treatment, or cure of disease, with the drugs including Alpha-1 anti-trypsin, Anti-Angiogenesis agents, Antisense, butorphanol, Calcitonin and analogs, Ceredase, COX-II inhibitors, dermatological agents, dihydroergotamine, Dopamine agonists and antagonists, Enkephalins and other opioid peptides, Epidermal growth factors, Erythropoietin and analogs, Follicle stimulating hormone, G-CSF, Glucagon, GM-CSF, granisetron, Growth hormone and analogs (including growth hormone releasing hormone), Growth hormone antagonists, Hirudin and Hirudin analogs such as hirulog, IgE suppressors, Insulin, insulinotropin and analogs, Insulin-like growth factors, Interferons, Interleukins, Leutenizing hormone, Leutenizing hormone releasing hormone and analogs, Low molecular weight heparin, M-CSF, metoclopramide, Midazolam, Monoclonal antibodies, Narcotic analgesics, nicotine, Non-steroid anti-inflammatory agents, Oligosaccharides, ondansetron, Parathyroid hormone and analogs, Parathyroid hormone antagonists, Prostaglandin antagonists, Prostaglandins, Recombinant soluble receptors, scopolamine, Serotonin agonists and antagonists, Sildenafil, Terbutaline, Thrombolytics, Tissue plasminogen activators, TNF-, and TNF-antagonist, the vaccines, with or without carriers/adjuvants, including prophylactics and therapeutic antigens (including but not limited to subunit protein, peptide and polysaccharide, polysaccharide conjugates, toxoids, genetic based vaccines, live attenuated, reassortant, inactivated, whole cells, viral and bacterial vectors) in connection with, addiction, arthritis, cholera, cocaine addiction, diphtheria, tetanus, HIB, Lyme disease, meningococcus, measles, mumps, rubella, varicella, yellow fever, Respiratory syncytial virus, tick borne japanese encephalitis, pneumococcus, *streptococcus*, typhoid, influenza, hepatitis, including hepatitis A, B, C and E, otitis media, rabies, polio, HIV, parainfluenza, rotavirus, Epstein Barr Virus, CMV, *chlamydia*, non-typeable haemophilus, moraxella catarrhalis, human papilloma virus, tuberculosis including BCG, gonorrhoea, asthma, atheroschlerosis malaria, *E-coli*, Alzheimer's, *H. Pylori, salmonella*, diabetes, cancer, herpes simplex, human papilloma and the like other substances including all of the major therapeutics such as agents for the common cold, Anti-addiction, anti-allergy, anti-emetics, anti-obesity, antiosteoporeteic, anti-infectives, analgesics, anesthetics, anorexics, antiarthritics, antiasthmatic agents, anticonvulsants, anti-depressants, antidiabetic agents, antihistamines, anti-inflammatory agents, antimigraine preparations, antimotion sickness preparations, antinauseants, antineoplastics, antiparkinsonism drugs, antipruritics, antipsychotics, antipyretics, anticholinergics, benzodiazepine antagonists, vasodilators, including general, coronary, peripheral and cerebral, bone stimulating agents, central nervous system stimulants, hormones, hypnotics, immunosuppressives, muscle relaxants, parasympatholytics, parasympathomimetrics, prostaglandins, proteins, peptides, polypeptides and other macromolecules, psychostimulants, sedatives, sexual hypofunction and tranquilizers and major diagnostics such as tuberculin and other hypersensitivity agents as described in U.S. Pat. No. 6,569,143, entitled "Method of Intradermally Injecting Substances", the entire content of which is expressly incorporated herein by reference.

Vaccine formulations which can be delivered in accordance with the systems and methods of aspects of the present invention can be selected from the group consisting of an antigen or antigenic composition capable of eliciting an immune response against a human pathogen, which antigen or antigenic composition is derived from HIV-1, (such as tat, nef, gp120 or gp160), human herpes viruses (HSV), such as gD or derivatives thereof or Immediate Early protein such as ICP27 from HSVI or HSV2, cytomegalovirus (CMV (esp. Human) (such as gB or derivatives thereof), Rotavirus (including live-attenuated viruses), Epstein Barr virus (such as gp350 or derivatives thereof), Varicella Zoster Virus (VZV, such as gpl, II and IE63) or from a hepatitis virus such as hepatitis B virus (for example Hepatitis B Surface antigen or a derivative thereof), hepatitis A virus (HAV), hepatitis C virus and hepatitis E virus, or from other viral pathogens, such as paramyxoviruses: Respiratory Syncytial virus (RSV, such as F and G proteins or derivatives thereof), parainfluenza virus, measles virus, mumps virus, human papilloma viruses (HPV for example HPV6, 11, 16, 18), flaviviruses (e. g. Yellow Fever Virus, Dengue Virus, Tick-borne encephalitis virus, Japanese Encephalitis Virus) or Influenza virus (whole live or inactivated virus, split influenza virus, grown in eggs or MDCK cells, or whole flu virosomes or purified or recombinant proteins thereof, such as HA, NP, NA, or M proteins, or combinations thereof), or derived from bacterial pathogens such as *Neisseria* spp, including *N. gonorrhea* and *N. meningitidis* (for example capsular polysaccharides and conjugates thereof, transferrin-binding proteins, lactoferrin binding proteins, PilC, adhesins); *S. pyogenes* (for example M proteins or fragments thereof, C5A protease, lipoteichoic acids), *S. agalactiae, S. mutans; H. ducreyi; Moraxella* spp, including *M catarrhalis*, also known as *Branhamella catarrhalis* (for example high and low molecular weight adhesins and invasins); *Bordetella* spp, including *B. pertussis* (for example pertactin, pertussis toxin or derivatives thereof, filamenteous hemagglutinin, adenylate cyclase, fimbriae), *B. parapertussis* and *B. bronchiseptica; Mycobacterium* spp., including *M. tuberculosis* (for example ESAT6, Antigen 85A, -B or-C), *M. bovis, M. leprae, M. avium, M. paratuberculosis M. smegmatis; Legionella* spp, including *l. pneumophila; Escherichia* spp, including enterotoxic *E. coli* (for example colonization factors, heat-labile toxin or derivatives thereof, heat-stable toxin or derivatives thereof), enterohemorragic *E. coli*, enteropathogenic *E. coli* (for example shiga toxin-like toxin or derivatives thereof); *Vibrio* spp, including *V. cholera* (for example cholera toxin or derivatives thereof); *Shigella* spp, including *S. sonnei, S. dysenteriae, S. flexnerii; Yersinia* spp, including *Y. enterocolitica* (for example a Yop protein), *Y. pestis, Y. pseudotuberculosis; Campylobacter* spp, including *C. jejuni* (for example toxins, adhesins and invasins) and *C. coli; Salmonella* spp, including *S. typhi, S. paratyphi, S. choleraesuis, S. enteritidis; Listeria* spp., including *L. monocytogenes; Helicobacter* spp, including *H. pylori* (for example urease, catalase, vacuolating toxin); *Pseudomonas* spp, including *P. aeruginosa; Staphylococcus* spp., including *S. aureus, S. Epidermidis; Enterococcus* spp., including *E. faecalis, E. faecium; Clostridium* spp., including *C. tetani* (for example tetanus toxin and derivative thereof), *C. botulinum* (for example Botulinum toxin and derivative thereof), *C. difficile* (for example clostridium toxins A or B and derivatives thereof); *Bacillus* spp., including *B. anthracis* (for example botulinum toxin and derivatives thereof); *Corynebacterium* spp., including *C. diphtheriae* (for example diphtheria toxin and derivatives thereof); *Borrelia* spp., including *B. Burgdorferi* (for example OspA, OspC, DbpA, DbpB), *B. garinii* (for example OspA, OspC, DbpA, DbpB), B. afzelii (for example OspA, OspC, DbpA, DbpB), *B. andersonii* (for example OspA, OspC, DbpA, DbpB), *B. Hermsii; Ehrlichia* spp., including *E. equi* and the agent of the Human Granulocytic Ehrlichiosis; *Rickettsia* spp, including *R. rickettsii; Chlamydia* spp., including *C. Trachomatis* (for example MOMP, heparin-binding proteins), *C. pneumoniae* (for example MOMP, heparin-binding proteins), *C. psittaci; Leptospira* spp., including *L. interrogans; Treponema* spp., including *T. pallidum* (for example the rare outer membrane proteins), *T. denticola, T. hyodysenteriae;* or derived from parasites such as *Plasmodium* spp., including *P. Falciparum; Toxoplasma* spp., including *T. gondii* (for example SAG2, SAG3, Tg34); *Entamoeba* spp., including *E. histolytica; Babesia* spp., including *B. microti; Trypanosoma* spp., including *T. cruzi; Giardia* spp., including *G. lamblia; Leshmania* spp., including *L. major; Pneumocystis* spp., including *P. Carinii; Trichomonas* spp., including *T. vaginalis; Schisostoma* spp., including *S. mansoni*, or derived from yeast such as *Candida* spp., including *C. albicans; Cryptococcus* spp., including *C. neoformans*, as described in PCT Patent Publication No. WO 02/083214, entitled "Vaccine Delivery System", the entire content of which is expressly incorporated herein by reference.

These also include other preferred specific antigens for *M. tuberculosis*, for example Tb Ra12, Tb H9, Tb Ra35, Tb38-1, Erd 14, DPV, MTI, MSL, mTTC2 and hTCC1. Proteins for *M. tuberculosis* also include fusion proteins and variants thereof where at least two, preferably three polypeptides of *M. tuberculosis* are fused into a larger protein. Preferred fusions include Ra12-TbH9-Ra35, Erd14-DPV-MTI, DPV-MTI-MSL, Erd14-DPV-MTI-MSL-mTCC2, Erd14-DPV-MTI-MSL, DPV-MTI-MSL-mTCC2, TbH9-DPV-MTI. Most preferred antigens for *Chlamydia* include for example the High Molecular Weight Protein (HWMP), ORF3, and putative membrane proteins (Pmps). Preferred bacterial vaccines comprise antigens derived from *Streptococcus* spp, including *S. pneumoniae* (for example capsular polysaccharides and conjugates thereof, PsaA, PspA, streptolysin, choline-binding proteins) and the protein antigen Pneumolysin (Biochem Biophys Acta, 1989,67,1007; Rubins et al., Microbial Pathogenesis, 25,337-342), and mutant detoxified derivatives thereof. Other preferred bacterial vaccines comprise antigens derived from *Haemophilus* spp., including *H. influenzae* type B ("Hib", for example PRP and conjugates thereof), non typeable *H. influenzae*, for example OMP26, high molecular weight adhesins, P5, P6, protein D and lipoprotein D, and fimbrin and fimbrin derived peptides or multiple copy variants or fusion proteins thereof. Derivatives of Hepatitis B Surface antigen are well known in the art and include, inter alia, PreS1, PreS2 S antigens. In one preferred aspect the vaccine formulation of the invention comprises the HIV-1 antigen, gp120, especially when expressed in CHO cells. In a further embodiment, the vaccine formulation of the invention comprises gD2t as hereinabove defined.

The embodiments of the present invention described herein include a push-surface (i.e. push button) design wherein the device can be positioned and affixed to a skin surface, and energized and/or activated by gently pressing a push button or push surface. Specifically, the user first removes the device from a sterile packaging and may also remove an adhesive cover (not shown) and/or a needle cap. Upon removal of the device from the package and prior to use, the features described above allows the user to inspect both the device and the contents therein, including inspection for missing or damaged components, expiration dates(s), hazy or color-shifted drugs, and so forth. After use, the user can once again inspect the device to ensure the entire dose was delivered. In this regard, the device can include an administered dose indicator for example, a readable gauge area that is at least 20% of the surface area of the device housing and accurate to within +/−10% of the labeled dose. The next step is the reconstitution step. The device can include a receiving port for the receipt of a drug container, which interacts with the contents of the reservoir within the housing to form a reconstituted medicament solution.

The next step is the positioning and application of the device to the user's skin surface. Like a patch, the user firmly presses the device onto the skin. The device includes a bottom surface having an adhesive layer to secure the device to the skin of the user. This bottom surface can be flat, contoured, or shaped in any suitable fashion, and includes an adhesive layer thereon, which would most likely be covered prior to shipping. Prior to use, the user peels back the adhesive covering, such as a film covering the adhesive, thereby exposing the adhesive for placement against the skin, if it has not already been removed in conjunction with the devices de-shielding or sterile package removal.

Once removed, the user is then able to place the device against the skin and press to ensure proper adhesion. As noted above, once properly positioned, the device may be activated by sliding the button or pressing a push surface. This activation step releases the Disk spring allowing it to press against the flexible film of the reservoir subassembly, pressurizing the reservoir. This activation step also may also serve to release the patient needle manifold and seat the patient needles. Finally, the activation step may also serve to open one or more of the valve assemblies described above, establishing a fluid communication path between the reservoir and the patient needles. A significant benefit to each embodiment described above includes the ability to achieve each step in a single push button action. Additionally, another significant benefit includes the use of a continuous fluid communication path comprised of the reservoir subassembly.

Once activated, the user typically leaves the device in position, or wears the device, for some period of time, such as ten minutes to seventy-two hours for complete delivery of the device contents, and then removes and discards the device with no damage to the underlying tissue. However, upon intentional or accidental removal, one or more safety features can deploy as described in greater detail in US Patent application of Cindrich et al., Ser. Nos. 10/916,649 and 10/916,648, filed on Aug. 12, 2004.

In addition to the performance advantages described above, another advantage of the embodiments described above is the ability to make two or more distinct, self-contained subassemblies that allow for assembly flexibility. Each subassembly is self-contained and stable, and provides the ability to separate the reservoir assembly or the cartridge assembly from remaining components, allowing separate filling and inspection of the reservoir and/or cartridge assembly, while preventing the unnecessary handling of the remaining components. Additionally, should any of the additional components be discarded, the costly reservoir contents can be spared and used in another assembly. Also, the reservoir contains no unnecessary parts and as a result, brings a low particle load into filling operations. Also, all stored energy components are in the body subassembly so they cannot be inadvertently deployed during filling of the reservoir. Specifically, no springs are included in the reservoir, which prevents the chance of unwanted spring release during filling.

Another aspect of the invention provides methods to reduce bubble formation upon product reconstitution by using at least a partial vacuum while the product is packaged as a dry form. It is theorized that dried products which contain some bubble forming components, e.g. surfactant, will upon product reconstitution, generate bubbles, especially when agitation is needed for reconstitution. For most applications, parenteral solutions must be free of all visible particulate material. Particles measuring 50 microns or larger can be detected by visual inspection. Specialized equipment is needed to detect particles less than 50 microns in size. The USP 27/NF 22 Section <788> sets limits on the number and size of particulates that are permissible in parenteral formulations. For small volume parenterals, the limit is 3000 particles/container that are equal to or larger than 10 microns, and not more than 300/container that are equal to or larger than 25 microns. Therefore, the healthcare professional or the patient need to make sure the solute is completely dissolved and the solution looks clear before administration. The presence of bubbles in the reconstituted solution can make the solution appear turbid, which in turn interferes with the observation and determination of complete dissolution of the product. The turbidity of the solution makes it very difficult to determine whether bubbles or insoluble particles are present. As previously mentioned, the latter would not be desirable in an injected product.

Additionally, injection of bubbles can cause serious problems as well. Therefore, healthcare professional and patient have to wait until bubbles dissipate and the solution looks transparent. It may take quite a long time for bubbles to dissipate especially in a viscous solution. Aspects of methods of present invention dictate that if the dried product is packaged and sealed under vacuum or partial vacuum, and if the vacuum is not completely released upon reconstitution (e.g. using a syringe to introduce diluent by punching into the stopper of a sealed vial), the vacuum helps to enhance the dissipation of bubbles. Details can be found in the following example.

EXAMPLE I

This example used a freeze dried formulation which contained 216 mg of an anti-HIV peptide, 200 mg PEG1500 and trace amount of sodium hydroxide and acetic acid in each vial for a desired pH. PEG 1500 helps enhance the solubility of the anti-HIV peptide. Upon reconstitution of this formulation, the freeze-dried cake wetted instantly and dissolved rapidly. Nevertheless dissolution of PEG 1500 generated large amounts of bubbles and these bubbles took approximately 20 min to dissipate. To prepare samples for the experiment, the formulation was reconstituted and reprocessed by freeze-drying and spray freeze-drying using 3 ml or 5 ml lyo vials. The vials were sealed under 2000 mT (partial vacuum) or atmospheric pressure. Then a dissolution test was performed and results can be found in Table 2. It was observed that a higher partial vacuum remaining in the vial after reconstitution reduces bubble formation. For instance, the product dissolution and bubble dissipation with the samples in the 5 ml vial was more rapid than those in the 3 ml vial and sealed under 2000 mT, despite that the sample amount in both vials were comparable. The volume effect of vials on bubble dissipation was unexpected, and it is theorized that the bigger vial provides more capacity to maintain higher partial vacuum than smaller vials after diluent was added. With the same vial size of 3 ml, the vials sealed under 2000 mT had less bubble formation than those sealed at 1 ATM. It is theorized that the vacuum helps the bubbles escape from the solution and therefore, the solution clears faster.

TABLE 2

Result of reconstitution test of freeze-dried and spray freeze-dried anti-HIV peptide and PEG 1500 formulations.

| Dry Powder Processing | Powder Weight (g) | Recons. Water For Injection volume (ul) | Purity | Visual Observation of Dissolution Properties, in minutes | | | Vacuum in vial | Vial type | Qualitative Bubble formation |
|---|---|---|---|---|---|---|---|---|---|
| | | | | Fully Wet (min) | Completely Dissolve (min) | Bubbles clear (min) | | | |
| Freeze Dried | 186 | 384 | 100% | <1 | ~10 | 20 | ATM | 3 ml Wheaton | +++ |
| | 214 | 443 | ND | <1 | ~10 | 18 | 2000 mT | 3 ml Wheaton | ++ |

TABLE 2-continued

Result of reconstitution test of freeze-dried and spray freeze-dried anti-HIV peptide and PEG 1500 formulations.

| Dry Powder Processing | Powder Weight (g) | Recons. Water For Injection volume (ul) | Purity | Fully Wet (min) | Visual Observation of Dissolution Properties, in minutes Completely Dissolve (min) | Bubbles clear (min) | Vacuum in vial | Vial type | Qualitative Bubble formation |
|---|---|---|---|---|---|---|---|---|---|
| | 211 | 436 | ND | <1 | ~10 | 18 | 2000 mT | 3 ml Wheaton | ++ |
| | 207 | 428 | ND | <1 | ~10 | 18 | 2000 mT | 3 ml Wheaton | ++ |
| Spray Freeze Dried | 184 | 381 | 100% | 3 | 12 | 15 | ATM | 3 ml Wheaton | +++ |
| | 174 | 359 | ND | <1 | 5 | 8 | 2000 mT | 5 ml Kimble | + |
| | 168 | 347 | ND | <1 | 8 | 11 | 2000 mT | 5 ml Kimble | + |
| | 133 | 276 | ND | <1 | 10 | 20 | ATM | 3 ml Wheaton | +++ |

Unlike prior art methods; the methods and devices of bubble reduction according to aspects of the present invention can be conveniently applied during small and large-scale product manufacturing and packaging. The vacuum may be applied during the initial bottle/vial sealing, as in the manufacturing of the drug container or cartridge. In another embodiment, the vacuum may be also induced by special device upon reconstitution.

EXAMPLE II

It may be desirable to maintain the pressure in the drug container below atmospheric pressure throughout the process of reconstitution of the medicament. For this purpose, initial evacuation of the container to a pressure less than about 50 Torr is expected to be adequate as the vapor pressure introduced by the diluent is minimal. The vapor pressure of water at 22 C is 20 Torr. Once mixed the vapor pressure of the reconstituted aqueous medicament would generally be lower.

For example, in a drug reservoir of 1 ml volume, and an initial pressure of 2 Torr, the ideal gas law allows an estimate of the expected final pressure:

$$P_1 V_1 = P_2 V_2$$

Filling the container with 0.99 ml diluent, the final pressure due to the initial gas in the reservoir ($P_2$) is:

$$2\,T \times 1\,ml = P_2 \times (1-0.99)\,ml$$

The total pressure can be estimated as the sum of the partial pressures from the initial gas in the reservoir and the diluent.

$$P^{total} = P^{vap} + P_2 = 20\,T + 2 \times 1/0.01 = 220\,T$$

As a second example, with 50 Torr initial pressure, adding 0.9 ml diluent:

$$P_2 = 20 + 50 \times 1/0.1 = 520\,T$$

In both examples, the final pressure remains sub atmospheric.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention. We claim:

What is claimed is:

1. A method for preparing a medicament prior to delivery into the body of a patient by injection into or through the skin of a patient, comprising:
    providing a first reservoir having a flexible, non-distensible membrane, the first reservoir containing a substance at a predetermined pressure;
    providing a needle in selective communication to said first reservoir;
    providing a second reservoir having a chamber with at least one movable wall, said chamber containing a fluid, said chamber having a pressure greater than said predetermined pressure;
    causing fluid communication to occur between said chamber and said first reservoir whereby said fluid communication allows said fluid to flow between said first reservoir and said chamber and co-mingling of said fluid and said substance to form said medicament;
    moving said at least one movable wall of said chamber whereby said moving forces said medicament to flow from said chamber into said first reservoir, whereby said medicament is prepared for injection;
    delaying pressurization of said first reservoir until substantially all of said medicament has been forced into said first reservoir; and
    pressurizing said first reservoir and infusing the medicament into the body of the patient through the needle from said first reservoir.

2. A method according to claim 1 wherein said predetermined pressure is greater than 2000 mT of vacuum.

3. A method according to claim 1 wherein said substance is a lyophilized powder.

4. A method according to claim 1 wherein said substance is a spray freeze-dried powder.

5. A method according to claim 1 wherein said substance is a liposome.

6. A method according to claim 1 wherein said substance is a substantially dry powder.

7. A method according to claim 1 wherein said co-mingling of said liquid and said substance to form said medicament occurs in an atmosphere substantially comprised of an inert gas.

8. The method according to claim 1, wherein said predetermined pressure is less than atmospheric pressure.

9. A method according to claim 8 wherein said substance is a lyophilized powder.

10. A method according to claim 8 wherein said substance is a spray freeze-dried powder.

11. A method according to claim 8 wherein said substance is a liposome.

12. A method according to claim 8 wherein said substance is a substantially dry powder.

13. A method for preparing a medicament prior to delivery into the body of a patient by injection into or through the skin of a patient, comprising:

provided a first reservoir having a flexible, non-distensible membrane, the first reservoir containing a liquid at a predetermined pressure;

providing a needle in selective communication to said first reservoir;

providing a second reservoir having a chamber with at least one movable wall, said chamber containing a substance, said chamber having a pressure less than said predetermined pressure;

causing fluid communication to occur between said chamber and said first reservoir whereby said fluid communication allows said liquid to flow between said first reservoir and said chamber and co-mingling of said liquid and said substance to form said medicament;

moving said at least one movable wall of said chamber whereby said moving forces said medicament to flow from said chamber into said first reservoir, whereby said medicament is prepared for injection;

delaying pressurization of said first reservoir until substantially all of said medicament has been forced into said first reservoir; and pressurizing said first reservoir and infusing the medicament into the body of the patient through the needle from said first reservoir.

* * * * *